US008815316B2

(12) United States Patent
Duan et al.

(10) Patent No.: US 8,815,316 B2
(45) Date of Patent: Aug. 26, 2014

(54) ENZYME PRODUCT FOR RUMINANTS

(75) Inventors: Zhiyong Duan, Guangdong (CN); Yongcai Liu, Guangdong (CN); Ye Lao, Guangdong (CN)

(73) Assignee: Kemin Industries (Zhuhai) Co., Ltd., Sanzao, Zhuhai (CN)

( * ) Notice: Subject to any disclaimer, the term of this patent is extended or adjusted under 35 U.S.C. 154(b) by 975 days.

(21) Appl. No.: 12/164,706

(22) Filed: Jun. 30, 2008

(65) Prior Publication Data

US 2009/0004327 A1 Jan. 1, 2009

Related U.S. Application Data

(60) Provisional application No. 60/937,840, filed on Jun. 29, 2007.

(51) Int. Cl.
*A23K 1/165* (2006.01)
*A23K 1/18* (2006.01)

(52) U.S. Cl.
CPC ............ *A23K 1/1656* (2013.01); *A23K 1/1813* (2013.01); *Y10S 426/805* (2013.01); *Y10S 426/807* (2013.01)
USPC ................... 426/53; 426/2; 426/805; 426/54; 426/18; 426/807

(58) Field of Classification Search
USPC ............ 424/442; 426/50, 53, 807, 54, 2, 805, 426/18
See application file for complete search history.

(56) References Cited

U.S. PATENT DOCUMENTS

| | | | |
|---|---|---|---|
| 5,612,055 A | | 3/1997 | Bedford et al. |
| 5,720,971 A | * | 2/1998 | Beauchemin et al. ........ 424/438 |
| 5,922,343 A | * | 7/1999 | Stucker .......................... 424/438 |
| 6,506,423 B2 | * | 1/2003 | Drouillard et al. ................ 426/2 |
| 6,562,340 B1 | * | 5/2003 | Bedford et al. ............. 424/94.61 |
| 2003/0060424 A1 | * | 3/2003 | Banks et al. ..................... 514/25 |
| 2004/0126459 A1 | * | 7/2004 | Raczek ............................ 426/61 |
| 2006/0193897 A1 | | 8/2006 | Bedford et al. |

OTHER PUBLICATIONS

Neal P. Martin et al. "Fiber digestibility and Starch content of corn silage", pp. 19-24, downloaded from www.extension.uidaho.edu/ . . . /2008Fiber%20Digestibility_Martin.pdf, presented at the Idaho Alfalfa and Forage Conference, Feb. 26-27, 2008.*
Longland et al. J. Nutr. Jul. 2006 vol. 136 No. 7 2099S-2102S.*
David J. Schingoethe, Gene A. Stageman and Royce J. Treacher, Response of Lactating Dairy Cows to a Cellulase and Xylanase Enzyme Mixture Applied to Forages at the Time of Feeding, 1999, J Dairy Sci, 82:996-1003, pp. 996-1003, U.S.
L. Kung, Jr., R.J. Treacher, G.A. Nauman, A.M. Smagala, K.M. Endres and M.A. Cohen, The Effect of Treating Forages with Fibrolytic Enzymes on its Nutritive Value and Lactation Performance of Dairy Cows, 2000, J Dairy Sco 83:115-122, pp. 115-122, U.S.
T.A. McAllister, H.D. Bae, G.A. Jones, and K.J. Cheng, Microbial Attachment and Feed Digestion in the Rumen, 1994, J. Anim. Sci. 72:3004-3018, pp. 3004-3018, Canada.
K.A. Beauchemin, L.M. Rode, M. Maekawa, D.P. Morgavi, and R. Kampen, Evaluation of a Nonstarch Polysaccharidase Feed Enzyme in Dairy Cow Diets, 2000 J Dairy Sci 83:543-553, pp. 543-553, Canada.
K.H. Menke, L. Raab, A. Salewski, H. Steingass, D. Frutz and W. Schneider, The estimation of the digestibility and metabolizable energy content of ruminant feedingstuffs from the gas production when they are incubated with rumen liquor in vitro, 1979 Cambridge University Press, pp. 217-222, Great Britain.
Karl Heinz Menke and Herbert Steingass, Estimation of the Energetic Feed Value Obtained From Chemical Analysis and in Vitro Gas Production Using Rumen Fluid, 1988, Animal Research and Development, 28:7-55, pp. 7-15.
P.J. Van Soest, J.B. Robertson, and B.A. Lewis, Symposium: Carbohydrate Methodology, Metabolism, and Nutritional Implications in Dairy Cattle, Methods for Dietary Fiber, Neutral Detergent Fiber, and Nonstarch Polysaccharides in Relation to Animal Nutrition, 1991 J Dairy Sci 74:3583-3597, pp. 3583-3597, U.S.
Peter Schofield and Alice N. Pell, Measurement and Kinetic Analysis of the Neutral Detergent-Soluble Carbohydrate Fraction of Legumes and Grasses, J. Anim. Sci. 1995 73:3455-3463, pp. 3455-3463, U.S.
K.A. Beauchemin, D. Colombatto, D.P. Morgavi and W.Z. Yang, Use of Exogenous Fibrolytic Enzymes to Improve Feed Utilization by Ruminants, J. Anim. Sci. 81 (E. Suppl. 2):E37-E47, pp. E37-E47, France, 2003.
K.A. Beauchemin, D. Colombatto, D.P. Morgavi, W.Z. Yang and L.M. Rode, Mode of action of exogenous cell wall degrading enzymes for ruminants, Canadian Journal of Animal Science, pp. 13-22, Canada, 2004.
K.A. Beauchemin, D. Colombatto, and D.P. Morgavi, A rationale for the development of feed enzyme products for ruminants, Canadian Journal of Animal Science, pp. 23-36, Canada, 2004.
L.B.Selinger, C.W. Forsberg and K.-J Cheng, The Rumen: A Unique Source of Enzymes for Enhancing Livestock Production, Minister of Public Works and Government Services Canada 1996, pp. 263-284, Canada.

* cited by examiner

*Primary Examiner* — Chhaya Sayala

(74) *Attorney, Agent, or Firm* — Davis, Brown, Koehn, Shors & Roberts, P.C.

(57) ABSTRACT

A method is described for improving the digestibility of a forage diet for ruminant animals. A forage, including alfalfa, Chinese wildrye, corn silage, straw silage, corn stover, ryegrass or TMR, is treated with an enzyme product having cellulase, xylanase, beta-glucanase, pectinase, mannanase and alpha-galactosidase activities.

4 Claims, 14 Drawing Sheets

ENZYME PRODUCT FOR RUMINANTS

This application claims priority to U.S. Patent Application Ser. No. 60/937,840, filed Jun. 29, 2007, which is incorporated herein by this reference.

BACKGROUND OF THE INVENTION

The present invention relates generally to ruminant nutrition and, more specifically, to the use of a mixture of enzymes in ruminant nutrition to improve the nutritive value of ruminant feedstuffs.

The stomach of ruminants is composed of four chambers: rumen, reticulum, omasum and abomasum. Among these four compartments, the rumen is the most important because most of the nutrients are digested in this chamber. The rumen is sacculated into dorsal, ventral, caudodosal, and caudoventral sacs. The sacculation increases the surface area for efficient absorption. Digestion in the rumen is a fermentation process, providing an anaerobic environment, constant temperature and pH, and good mixing. The fermentation process is accomplished by a profound culture of bacteria, each of which plays a different role in digestion, such as cellulolysis, hemicellulolysis, proteolysis, acid production, methane production, vitamin synthesis, etc. The products from fermentation are either absorbed in the rumen itself or flow out for further digestion and absorption downstream. In addition to the rumen, the abomasum is another important compartment. The abomasum is a "true stomach" which is very similar to the stomach in monogastric animals. It secretes acid to maintain acidic environment. Different from the stomach in monogastric animals, the abomasum secretes lysozyme and therefore is capable of digesting bacteria.

The diet of ruminants typically consists of concentrate and roughage. Roughage usually refers to forage and silage. Forage refers to grasses, legumes, browseable trees and fibrous crop byproducts. Major nutrients in this diet include starch, fiber, protein, fat and oil. Starch is usually degraded either in the rumen or in the abomasum, while fiber, protein, and fat/oil are generally degraded in the rumen by ruminal bacteria. Fiber is digested by cellulolytic and hemicellulolytic bacteria and turned into volatile fatty acids (VFA). Protein either bypasses the rumen or is degraded by proteolytic bacteria and converted into microbial protein which ultimately is utilized by the abomasum. Fat/oil is converted by lipase to fatty acids which are absorbed by the ruminal wall.

As a major component of a typical ruminant diet, forage usually refers to grasses, legumes and fibrous crop byproducts such as rice straw and corn straw. The efficiency of converting forages to productivity is limited by the digestibility of forage cell walls. Plant cell walls usually account for 40-70% of the dry matter of typical forages and, even under ideal conditions, cell wall digestibility in the total digestive tract is generally still less than 65%. Therefore, forage digestibility becomes the bottleneck for the energy availability and causes animals fail to achieve optimal productivity. To make things worse, due to the shortage of high-quality forage, low quality forage is often used to feed ruminants. Because the low quality forage has very little nutritional value, the productivity of ruminant livestock is further limited.

In recent years there have been several attempts to improve the digestibility of forage. A limited number of ruminant enzymes products are commercially available. Many of these enzyme products were merely derivatives of monogastric counterparts, while others manifest unpredictable efficiency. However, researchers have not been successful at using enzymes to enhance the utilization of ruminant diets, partially because of the perceptions that the hydrolytic capacity of the rumen could not be enhanced by supplemental enzymes, and the concerns that such enzymes would be ineffective due to ruminal proteolysis. These misconceptions have been disproved by some recent studies. A couple of researches have shown that adding exogenous fibrolytic enzymes to ruminant diets increased milk production (Schingoethe et al., 1999; Kung et al., 2000) and average daily gain (ADG) (McAllister et al., 1999) in some cases. These cases of improved animal performance were due to the increased feed digestion. Numerous studies have reported increased digestion of dry matter (DM) and fiber measured by in situ and in vitro methods (Beauchemin et al., 2000; Kung et al., 2000).

However, cellulase and xylanase alone are not sufficient to exert the best potential for ruminants. Some other factors, including beta-glucanase, pectinase, mannanase and alpha-galactosidase can be limiting factors. Therefore, it is very important to include these enzymes to release the energy in cell wall of plants.

Some companies advertise their products as dairy specific or ruminant specific. However, these products have two flaws. Firstly, almost all of their products contain amylase. As other animals, ruminants require glucose for normal physiological functions. Starch is usually metabolized either into volatile fatty acid in rumen or into glucose in abmason. If starch is digested too fast in the rumen and leave very little starch for the abmason to generate glucose, ruminants may have insufficient glucose to meet normal biological requirements. Therefore, it is preferable that starch bypass the rumen and be digested in the abmason. For this reason, amylase should not be contained in the feed additive for ruminants. As a matter of fact, some farmers even use amylase inhibitor to help starch to bypass the rumen. Moreover, inclusion of amylase in the rumen additive may cause acidosis. Secondly, these products do not have a complete enzyme profile. There is a need for a product that contains beta-glucanase, pectinase, mannanase and alpha galactosidase, in addition to xylanase and cellulase which are well known as enzyme additives for ruminants. Ruminants consume a lot of legume and grass, so these enzymes are important for ideal digestibility. However, these enzymes are missing in the current products on the market.

Therefore, there is a need for an enzyme product that improves the digestibility of fiber on the basis of most common ruminant diets.

SUMMARY OF THE INVENTION

The present invention consists of an enzyme product that removes or reduces the limiting factors in fiber to improve the digestibility of fiber in forage. This enzyme product represents a unique combination of several cellulolytic and hemicellulolytic enzymes. This enzyme product significantly improves digestion of commonly used forage diets in ruminal condition. In a preferred embodiment of the invention, a gram of the enzyme product contains between about 200 and about 800 units of activity of cellulase, between about 750 and about 3000 units of activity of xylanase, between about 225 and about 890 units of activity of beta-glucanase, between about 1 and about 100 units of activity of pectinase, between about 50 and about 800 units of activity of beta-mannanase, and between about 1 and about 100 units of activity of alpha-galactosidase. A more preferred embodiment of the invention contains, per gram of product, between about 200 and about 600 units of activity of cellulase, between about 750 and about 2250 units of activity of xylanase, between about 225 and about 625 units of activity of beta-glucanase, between about 1 and about 5 units of activity of pectinase, between about 100 and about 300 units of activity of beta-mannanase, and between about 1 and about 5 units of activity of alpha-galactosidase.

An object of the invention is to reduce or eliminate the limiting factors in fiber digestion and release more energy.

Another object of the invention is to exclude amylase, which has been reported to improve energy usage, help maintaining normal glucose levels, and reduce the possibility of acidosis.

DETAILED DESCRIPTION OF PREFERRED EMBODIMENTS

Figure 1:
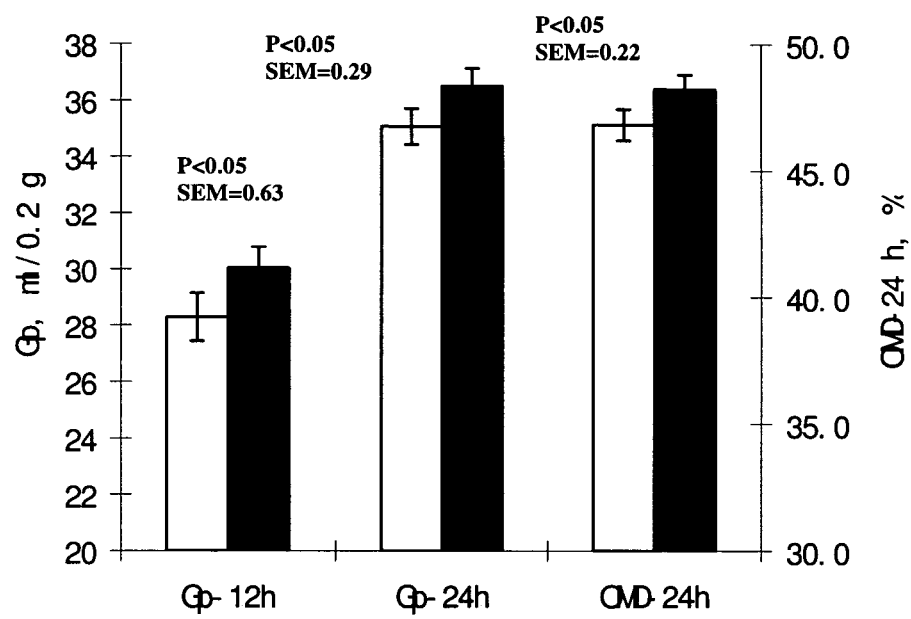
FIG. 1 is a graph of the effects of a preferred embodiment of the invention on the gas production (Gp) at 12 h and 24 h and organic matter digestibility (OMD) at 24 h in vitro of alfalfa; the control (left columns) was blank with no enzyme treated; the dosage of treatment (right columns) was 1000 g/T.

The present invention provides an enzyme product that is suitable for use in dairy feed in order to improve forage digestion.

The enzyme products are produced from a combination of cellulase, xylanase, pectinase, beta-glucanase, mannanase and alpha-galactosidase. Other ingredients in the product can include, but are not restricted to, carriers, flavors and enzyme stabilizing compounds.

The enzyme ingredients that are used in the process can be either liquid or solid. Solid enzymes can be directly mixed with the other ingredients. Liquid enzymes can be sprayed onto a carrier first and then mixed with the other ingredients.

The enzyme product can be applied to a seed concentrate before mixing with forage.

The enzyme product can be applied, to rations for dairy cattle, sheep, lamb and goats.

The preferred dosage of this enzyme product depends on the ruminant diet. Those skilled in the art will recognize that the dosage is dependent on the percentage of fiber in diet and the composition of fiber. Typical dosage is between 100-2000 g/ton of forage being treated. In a preferred embodiment the final application of product is between 300,000 and 12,000,000 units of enzyme activity for each ton of diet.

This enzyme may optionally be applied, as a feed additive into the feed concentrate for a ruminant, as an ingredient during the mixing of a total mixed ration (TMR), or as a component during the mixing of homemade complete feeds.

In a preferred embodiment of the invention, a gram of the enzyme product contains between about 200 and about 800 units of activity of cellulase, between about 750 and about 3000 units of activity of xylanase, between about 225 and about 890 units of activity of beta-glucanase, between about 1 and about 100 units of activity of pectinase, between about 50 and about 800 units of activity of beta-mannanase, and between about 1 and about 100 units of activity of alpha-galactosidase. A more preferred embodiment of the invention contains, per gram of enzyme product, between about 200 and about 600 units of activity of cellulase, between about 750 and about 2250 units of activity of xylanase, between about 225 and about 625 units of activity of beta-glucanase, between about 1 and about 5 units of activity of pectinase, between about 100 and about 300 units of activity of beta-mannanase, and between about 1 and about 5 units of activity of alpha-galactosidase. Enzyme products with activities of the enzyme components between these ranges have been made and tested.

In Vitro Evaluation

The effect of enzyme product in this invention was determined relative to a standard series of feed samples which were not treated.

The in vitro method established by Menke et al. in 1979 and developed in 1988 is a classical method to simulate the in vivo digestion process occurred. In this method, ruminal fluid is obtained from cannulated ruminant animal and incubated with substrate diet under certain conditions. Since there is a high correlation found between gas production in vitro and digestibility in vivo in this method (Menke et al., 1979; Menke et al. 1988), gas production is measured as an indication of the level of digestibility and metabolizable energy content. The method has demonstrated a high level of consistency between the gas production and in vivo animal performance. During the last two decades, this method has been widely applied to evaluate the nutritional values of forage.

Three fully-grown sheep were used as donor animals and fitted with a rumen cannula. All the three donor animals were fed by the same diet (30% of concentrates and 70% of hay) during the same time (8:30, am; 4:30, pm). A daytime interval of 8 hours or longer is needed before the rumen fluid was collected. The ingredients and chemical composition of the experimental diets for donor sheep are given in Table 1.

TABLE 1

Ingredients and chemical composition of the experimental diets for donor sheep

| Ingredients | Ratio |
|---|---|
| Concentration supplement, % | |
| Corn | 50.0 |
| Bran | 15.0 |
| Soy bean | 10.0 |
| Rapeseed bean | 9.0 |
| $NaHCO_3$ | 10.0 |
| NaCl | 1.5 |
| $Ca(HCO_3)$ | 21.0 |
| $CaCO_3$ | 1.5 |
| Vitamin premix | 1.9 |
| Chemical composition | 0.1 |
| Concentration supplement | |
| Moisture, % | 13.5 |
| CP, % | 14.7 |
| Ca*, % | 1.6 |
| P*, % | 0.8 |
| NE*, NND | 2.3 |
| Chinese wild rye, % | |
| Moisture | 8.7 |
| CP | 6.6 |
| NDF | 59.3 |
| OMD | 95.5 |

*Calculated values, and the others are measured values

Rumen fluid was collected and treated as described by Menke et al. (1988). In brief, rumen fluid was collected from three rumen-cannulated sheep before the morning feeding. A suction bottle (about 2 L) was used to collect the fluid. The bottle was sealed with a rubber stopper with a hole in the middle and connected via a tube to a slightly bent PVC pipe (about 10 mm in diameter). The pipe, which has about ten small holes at the far end, was introduced through the rumen cannula into the rumen. A manually-operated vacuum pump was used to suck out the rumen fluid from rumen.

The rumen fluid from the three sheep was mixed with an anaerobic buffer/mineral solutions (1:2, v/v) as described by Menke et al. (1988), taken to the laboratory in a water bath pre-heated to 39° C., filtered through four layers of cheesecloth, and stored in a warm insulated flask filled with $CO_2$. Enzyme-supplemented samples (200 mg, DM) were incubated in 100 ml syringes filled with 30 ml buffered rumen fluid in a shaking water bath at 39° C. The blank sample with no enzyme supplementation was used as control. Two runs of incubation were carried out, with triplicate in each run. The gas production was recorded at 0, 2, 4, 6, 9, 12 and 24 h.

Organic matter digestibility at 24 h (OMD24 h) of substrate was calculated from gas production at 24 h with the equation given by Menke:

$$OMD24\ h, \% = 0.986 \times Gp24\ h + 0.0606 \times CP\ \% + 11.3$$

where OMD24 h, Gp24 h and CP are the organic matter digestibility at 24 h, the gas production at 24 h and the crude protein content of substrate, respectively.

The data were compared by T test using the statistical software SAS (v 6.12, 1996). Difference was declared when $p<0.05$ and significant difference was declared when $p<0.01$.

In the first round of incubation, an imitated total mixture ration (TMR) of dairy cows was used to study the effect of enzymes on the digestion of TMR. The ingredients of the imitated TMR are described Table 2.

TABLE 2

Ingredients of imitated TMR

| Ingredients | Ratio, % |
|---|---|
| Alfalfa meal | 50.0 |
| Corn meal | 30.0 |
| Soybean meal | 20.0 |
| Total | 100.0 |

Pure NDF was used as substrate in the second round to study the effect of enzyme formulas on the digestion of fiber. NDF was extracted from ryegrass as described by Robertson and Van Soest (1981) and Van Soest et al. (1991). Briefly, ryegrass was treated by amylase followed by washing with neutral detergent. The extracted NDF was immersed in IM ammonium sulfate $((NH_4)_2SO_4)$ solution at 39° C. overnight in order to remove ionic traces of detergent (Schofield and Pell, 1995). The samples were then washed stepwise in hot water and ethanol, filtered in crucibles with porous discs and oven-dried at 50° C.

Activities of cellulase, xylanase, beta-glucanase, pectinase, mannanase and alpha-galactosidase were determined by methods WI-KAE-021, WI-KAE-022 and KCCM-005 (see Enzyme Assays below). So-called ruminal methods were used for Tables 5, 7, 9 and 11. Ruminal methods were the same as the corresponding above-identified methods except for the conditions of incubation (using 39° C. and pH 6.0) in ruminal methods.

Preparation of enzyme samples Four preliminary enzyme formulas, termed KAC023-001, KAC023-002, KAC023-003 and KAC023-004 were prepared in the lab for the first round of fermentation. The main enzyme activities are presented in Table 3. Enzymes were added into the substrate at dosages of 0.5 g/Kg, 1.0 g/Kg and 2.0 g/Kg.

TABLE 3

Activities of individual enzymes, U/g

|  | KAC023-001 | KAC023-002 | KAC023-003 | KAC023-004 |
|---|---|---|---|---|
| Cellulase | 1000 | 1000 | 1000 | 1000 |
| Xylanase | 4000 | 4000 | 4000 | 4000 |
| β-Glucanase | — | 400 | — | 400 |
| Pectinase | — | — | 200 | 200 |

Based on the results from the first round of fermentation, the best formula KAC023-004 was selected and further optimized into two new formulas, KAC023-005 and KAC023-006. The main enzyme activities are given in Table 4. Samples were added to pure ryegrass NDF at the dosage of 1.0 g/Kg and incubated in the in vitro gas production with a blank control.

TABLE 4

Enzyme activities of samples used in the second round of test, U/g

|  | KAC023-005 | KAC023-006 |
|---|---|---|
| Cellulase | 2000 | 2800 |
| Xylanase | 10000 | 10000 |
| B-Glucanase | 400 | 400 |
| Pectinase | 200 | 200 |
| B-Mannonase | 200 | 200 |
| A-Galactosidase | present | present |

The stability of cellulase and xylanase in the rumen were determined in a similar way as gas production test, except that the dosage used was significantly higher (100 kg/T) in order to minimize noise from the endogenous enzyme activities. Substrates with KAC023-005 or KAC023-006 were incubated with rumen fluid. The activities of these two enzymes were determined at 0, 1, 2, 4, 6 and 12 h. Ratios of residual activity to initial activity, which were used to reflect the enzyme stability in rumen, were calculated according the equation below. Ratios, %=(At−A0)×100/At Where, At and A0 are the enzyme activities at t h and 0 h.

Enzyme Assays

Method WI-KAE-022

Mannanase is an enzyme capable of cleaving polyose chains containing mannose units. Mannanase enzyme hydrolyses the Locust bean gum mannan substrate to the reducing sugar units. The reducing sugars are reacted with 3,5 dinitrisalicylic acid (DNS). The color change produced is proportional to the amount of reducing sugar released (expressed as mannose), which in turn is proportional to the activity of mannanase present in the sample.

A 50 nM sodium citrate buffer solution is prepared by dissolving 14.7 g (+/−0.01 g) of tri-sodium citrate in 900 ml of demineralized water followed by dilution to 1000 ml with demineralized water. A 50 mM citric acid buffer solution is prepared by dissolving 10.5 g (+/−0.0 μg) of citric acid monohydrate in 900 ml of demineralized water followed by dilution to 1000 ml with demineralized water. A 0.5% (w/v) Locust bean gum mannan substrate is prepared by dissolving 0.5 g of Sigma Locust bean gum mannan in 70 ml of citric acid buffer (pH 5.3) followed by stirring for 20 minutes or until the mannan is completely dissolved. Dilute to 100 ml with sodium citrate buffer (pH 5.3) and check that the final pH of the substrate solution is 5.3 (+/−0.05). A 3,5 dinitrisalicylic acid (DNS) 100 ml solution is made by dissolving 1.6 g of sodium hydroxide in 70 ml demineralized water in an ambient bottle. Add 1 g of 3,5 dinitrosalicylic acid (DNS) followed by 30 g potassium sodium tartarate and dilute to 100 ml with demineralized water. The DNS solution can be stored for 1 month at room temperature. A mannose stock solution 1000 μg/ml is prepared by dissolving 0.1 g (+/−0.001 g) of mannose with 50 mM sodium citrate buffer (pH 5.3) and topping up to 100 ml using a 100 ml volumetric flask. Standard mannose solutions containing between 0 and 500 μg/ml (in 50 μg/ml increments) are prepared by diluting an appropriate amount of the stock mannose solution with sodium citrate buffer.

Extract X g (+/−0.01 g) of the sample in Y ml buffer for 10 minutes on a magnetic stirrer (beaker). Centrifuge to obtain a clear enzyme solution (>1,700 g, 5 minutes). The solution is diluted Z times in buffer. Pipette 0.9 ml of 0.5% substrate solution into a test tube (each sample should be assayed twice). Incubate this mix in a water bath at 50° C. for two minutes. Start the timer and immediately add 0.1 ml enzyme solution into the test tubes at 30 seconds intervals. Shake each tube well on a Vortex mixer and replace the tube in the water bath. Incubate the test tubes for exactly 10 minutes in the water bath at 50° C. Stop the reaction at 30 seconds intervals by adding 1.5 ml DNS solution and shake well to stop the reaction. In the control tube, the enzyme solution is added after the addition of the DNS solution. For mannose standards, pipette 1000 μl into each test tube followed by addition of 1.0 ml DNS. Place the tubes for 5 minutes in a boiling water bath (100° C.). Cool and read the optical density at 540 nm.

One unit of activity is the amount of enzyme that releases 1 mg mannose from mannan per 60 minutes under the given assay conditions $$U/g = \frac{\text{mg mannose} * f * 10 * 60}{10}$$

wherein f=dilution factor=Y×Z×1/X.

Method WI-KAE-005

Alpha-galactosidase releases p-nitrophenol from pNP-alpha-D-galactopyranoside. The amount of liberated p-nitrophenol can be determined spectrophotometrically and is a measure for the alpha-galactosidase activity.

A sodium citrate buffer solution (pH 5.5, 0.25 M) is prepared by dissolving 18.45 g (+/−0.01 g) trisodium citrate and 2.62 g (+/−0.01 g) citric acid in 225 ml demineralized water. Check the pH (5.5±0.1) and adjust if necessary with NaOH or citric acid. Dilute to 250 ml with demineralized water. Discard when pH changes more than 0.05 units from the desired pH. A solution of p-nitrophenyl-alpha-D-galactopyranoside is prepared by dissolving 15 (±0.1) mg p-nitrophenyl-alpha-D-galactopyranoside in 5 ml demineralized water. A 5% $Na_2CO_3$ solution is prepared by dissolving 5 g (+/−0.01 g) $Na_2CO_3$ in 100 ml demineralized water.

Extract X g (+/−0.01 g) of the sample in Y ml buffer for 10 minutes on a magnetic stirrer. Centrifuge to obtain a clear enzyme solution (>1,700 g, 5 minutes). The solution is diluted Z times in buffer. Put into a test tube 1 ml sodium citrate buffer, 0.2 ml 0.01 M pNP-alpha-D-galactopyranoside, and 0.4 ml demineralized water. Incubate this mix in a water bath at 37° C. for five minutes. Start the timer and immediately add 0.4 ml enzyme solution into the test tubes at 30 seconds intervals. Shake each tube well on a vortex mixer and replace the tube in the water bath. Incubate the test tubes for exactly 15 minutes in the water bath at 37° C. Stop the reaction at 30 seconds intervals by adding 2 ml $Na_2CO_3$ 5% solution and shake well to stop the reaction. In the control tube, the enzyme solution is added after the addition of the $Na_2CO_3$ solution. Read the absorption at 410 nm against water.

One unit of activity is the amount of enzyme that releases 1 µmol p-nitrophenol from pNP-alpha-D-galactopyranoside per minute under the given assay conditions. The molar extinction coefficient of p-nitrophenol is 18240 $M^{-1}cm^{-1}$.

$$\epsilon_m = A/C*1 = 18240\ M^{-1}cm^{-1}$$

wherein A is the absorption, C is the molar concentration and 1 is the path length.

$$U/g = (A_{sample} - A_{blank})*36.55*f/1000$$

wherein f=dilution factor=Y×Z×1/X.

Method WI-KAE-021

Beta-glucanase reacts with beta-glucan to release glucose. Cellulase complex hydrolyses cellulose to a low molecular weight, reducing carbohydrates, primarily glucose and cellobiose. Pentosanase (xylanase) hydrolyses xylan. Pectinase hydrolyses pectin. Invertase cleaves sucrose molecules into fructose and glucose, which are reducing sugars. The reducing sugars formed are then determined according to the Somogyi-Nelson procedure.

Reaction Conditions

TABLE A

| Enzyme Activity | Buffer | | Temperature | Reaction time |
|---|---|---|---|---|
| Xylanase | Citric Acid buffer | - pH 5.3 (0.05 M) | 50° C. | 15 mins |
| Cellulase | Acetate buffer | - pH 4.8 (0.1 M) | 50° C. | 20 mins |
| Beta-glucanase | Phosphate buffer | - pH 7.5 (0.1 M) | 37° C. | 30 mins |
| Pectinase | Citric Acid buffer | - pH 4.0 (0.05 M) | 37° C. | 15 mins |

Nelson's reagent A (1000 ml) is prepared by dissolving 25.0 g sodium carbonate (anhydrous), 25.0 g potassium sodium tartrate tetrahydrate, 20.0 g sodium hydrogen carbonate, and 200.0 g sodium sulfate (anhydrous) in 950 ml demineralized water and diluted to 1000 ml.

Nelson's reagent B (100 ml) is prepared by dissolving 15.0 g copper (II) sulfate pentahydrate in 100 ml of demineralized water. Two drops of concentrated sulfuric acid, $H_2SO_4$ are added.

Nelson's reagent C (26 ml) is prepared by mixing 25 ml Nelson's reagent A with 1 ml Nelson's reagent B in a beaker.

Nelson's color reagent (arsenomolybdate) (1000 ml) is prepared by dissolving 50.0 g ammonium hepta-molybdate-tetrahydrate in 800 ml of demineralized water. Add 42 ml of concentrated sulfuric acid, $H_2SO_4$. Dissolve 6.0 g arsenic acid sodium ($Na_2HAsO_4.7H_2O$) in 50 ml of demineralized water and add to the molybdate solution. Top up to 1000 ml demineralized water using a volumetric flask. The reagent should be yellow with no green tint.

Beta Glucanase Assay

Extract X g (+/−0.01 g) of the sample in Y ml buffer for 10 minutes on a magnetic stirrer (beaker). Centrifuge to obtain a clear enzyme solution (>1,700 g, 5 minutes). The solution is diluted Z times in buffer. Pipette 1 mL of the final solution into a test tube. The blank remains empty for now. Determinations of samples are made in duplicate. Pipette 1 mL of each standard in the corresponding tubes, with demineralized water as the zero standard. Preheat the test tubes in the water bath at exactly 37° C. for 5 minutes. Add 1 ml beta-glucan substrate 0.5% to each tube at 30 seconds intervals. Shake each tube well on a vortex mixer, and replace the tube in the water bath at 37° C. Incubate the tubes for exactly 30 minutes at 37° C. Add 1 ml Nelson's reagent C to each tube at 30 seconds intervals and shake well to stop the reaction. Add 1 ml of the sample's final solution into the sample blank tubes and shake them well. Place the tubes for 20 minutes in a boiling water bath (100° C.). Cool and add 1 ml Nelson's color reagent to all the test tubes and shake well on a vortex mixer. Add 5 ml demineralized water to each tube and shake well on a vortex mixer. Centrifuge to obtain a clear enzyme solution (>1,700 g, 5 minutes). Read the optical density at 540 nm.

Cellulase Assay

Extract X g (+/−0.01 g) of the sample in Y ml buffer for 10 minutes on a magnetic stirrer (beaker). Centrifuge to obtain a clear enzyme solution (>1,700 g, 5 minutes). The solution is diluted Z times in buffer. Pipette 1 ml of the final solution into a test tube. The blank remains empty for now. Determinations of samples are made in duplicate. Pipette 1 ml of each standard into the corresponding tubes, with demineralized water as the zero standard. Do not preheat test tubes. Add 1 ml CMC substrate to each tube at 30 seconds intervals. Shake each tube well on a Vortex mixer. Place the tube in a water bath of 50° C. Incubate the tubes exactly 20 minutes at 50° C. Add 1 ml Nelson's reagent C to each tube at 30 seconds intervals and shake well to stop the reaction. Add 1 ml of the sample's final dilution into the sample blank tubes and shake well. Place the tubes for 20 minutes in a boiling water bath. Cool and add 1 ml Nelson's color reagent to all the test tubes and shake well on a vortex mixer. Add 5 ml $H_2O$ to each tube and shake well on a Vortex mixer. Centrifuge to obtain a clear enzyme solution (>1,700 g, 5 minutes). Read the optical density at 540 nm.

Xylanase Assay

Extract X g (+/−0.01 g) of the sample in Y ml buffer for 10 minutes on a magnetic stirrer (beaker). Centrifuge to obtain a clear enzyme solution (>1,700 g on a centrifuge machine), 5 minutes. The solution is diluted Z times in buffer. Pipette 1 ml of the final solution into a test tube. The blank remains empty for now. Determinations of samples are made in duplicate. Pipette 1 ml of each standard in the corresponding tubes, with demineralized water as the zero standard. Do not preheat tubes. Add 1 ml xylan substrate 0.5% to each tube at 30 seconds intervals. Shake each tube well on a Vortex mixer, and replace the tube in the water bath at 50° C. Incubate the tubes for exactly 15 minutes at 50° C. Add 1 ml Nelson's reagent C to each tube at 30 seconds intervals and shake well to stop the reaction. Add 1 ml of the final solution into the sample blank tubes and shake them well. Place the tubes for 20 minutes in a boiling water bath (100° C.). Cool and add 1 ml Nelson's color reagent to all the test tubes and shake well on a Vortex mixer. Add 5 ml demineralized water to each tube and shake well on a Vortex mixer. Centrifuge to obtain a clear enzyme solution (>1,700 g, 5 minutes). Read the optical density at 540 nm.

Pectinase Assay

Extract X g (+/−0.01 g) of the sample in Y ml buffer for 10 minutes on a magnetic stirrer (NB: For lipid-coated enzymes such as Ronozyme VP (CT), add 5 drops of 10% Tween 20 solution and stir for 5 minutes. Then sonicate for 15 minutes before stirring sample for another 5 min). Centrifuge to obtain a clear enzyme solution (>1,700 g, 5 minutes). The solution is diluted Z times in buffer. Pipette 1 ml of the final solution into a test tube. The blank remains empty for now. Determinations of samples are made in duplicate. Pipette 1 ml of each standard in the corresponding tubes, with demineralized water as the zero standard. Preheat the test tubes in the water bath at exactly 37° C. for 5 minutes. Add 1 ml substrate solution to each tube at 30 seconds intervals. Shake each tube well on a Vortex mixer, and replace the tube in the water bath at 37° C. Incubate the tubes for exactly 15 minutes at 37° C. Add 1 ml Nelson's reagent C to each tube at 30 seconds intervals and shake well to stop the reaction. Add 1 ml of the final solution into the sample blank tubes and shake them well. Place the tubes for 20 minutes in a boiling water bath (100° C.). Cool and add 1 ml Nelson's color reagent to all the test tubes and shake well on a Vortex mixer. Add 5 ml demineralized water to each tube and shake well on a Vortex mixer. Centrifuge to obtain a clear enzyme solution (>1,700 g, 5 minutes). Read the optical density at 540 nm.

Calculations

One unit of activity is equivalent to the quantity of enzyme that liberates 1 μg of sugar-equivalent per minute under the conditions specified in this assay. A standard curve based on the results of the standard samples is plotted and the amount of sugar equivalents from the curve is determined.

The dilution factors should give reaction absorbance between the following for each activity respectively to remain within the linear region of the assay.

| Enzyme Activity | Absorbance Range |
|---|---|
| Xylanase | 0.200-1.000 |
| Cellulase | 0.200-0.500 |
| Beta-glucanase | 0.200-0.650 |
| Pectinase | 0.100-0.650 |

Pectinase

Reagent Blank Absorbance should be less than 0.02 in order to obtain accurate results. Dilute sample and repeat assay if it is greater than 0.02, unless absorbance of sample are below 0.100. Point 2 will not be applied when Asplelase F and its finished products are being analyzed due to the present of reducing sugar in the raw material.

Xylanase Activity:

Dissolve 10.51 g citric acid in 950 ml of demineralized water. Adjust to pH 5.3 with NaOH 10 M. Dilute to 1 L with demineralized water using a volumetric flask. Discard the buffer solution when pH changes more than 0.05 units from the desired pH.

Xylan Substrate (0.5%)

Weigh 0.50 g (+/−0.01 g) Birchwood xylan (Sigma X-0502) and add 100 ml citric acid buffer pH 5.3 solution. Boil this solution for 10 minutes while stirring. Cool the substrate to 50° C. Suggested storage time is 1 day.

D (+)-Xylose Stock Solution 1000 μg/ml

Dissolve 0.1 g (+/−0.001 g) of anhydrous Xylose with demineralized water and top up to 100 ml using a 100 ml volumetric flask.

Xylose Standards Solutions

Dilute the Xylose stock solution as follows:

| | Diluted stock solution | |
| Xylose (μg/ml) | 1000 μg/ml | Demineralized water |
|---|---|---|
| 0 | 0 ml | 1 ml |
| 40 | 4 ml | Dilute to 100 ml |
| 80 | 8 ml | Dilute to 100 ml |
| 120 | 12 ml | Dilute to 100 ml |
| 160 | 16 ml | Dilute to 100 ml |

Cellulase Activity:

Dissolve either 7.90 g sodium acetate trihydrate or 4.1 g sodium acetate anhydrous in 950 ml of demineralized water. Adjust the pH with glacial acetic acid to pH 4.8. Dilute to 1 L with demineralized water using a volumetric flask. Discard the buffer solution when pH changes more than 0.05 units from the desired pH.

CMC-Substrate (carboxymethylcellulose)

Add 0.40 g (+/−0.001 g) of CMC powder slowly to 100 ml acetate buffer pH 4.8 solution. Stir at room temperature until fully dissolved. Suggested storage time: 2 weeks in the refrigerator. Before use, heat the substrate for 25 minutes at 90° C. and cool to 50° C.

Glucose Stock Solution (1000 μg/ml)

Dissolve 0.1 g (+/−0.001 g) of anhydrous glucose with demineralized water and top up to 100 ml using a 100 ml volumetric flask.

Glucose Standard Solutions

Dilute the glucose stock solution as follow:

| | Diluted stock solution | |
| Glucose (μg/ml) | 1000 μg/ml | Demineralized water |
|---|---|---|
| 0 | 0 ml | 1 ml |
| 10 | 1 ml | Dilute to 100 ml |
| 20 | 2 ml | Dilute to 100 ml |
| 30 | 3 ml | Dilute to 100 ml |
| 40 | 4 ml | Dilute to 100 ml |
| 50 | 5 ml | Dilute to 100 ml |

Beta Glucanase Activity:

Dissolve 2.35 g potassium dihydrogen phosphate and 14.72 g di-sodium hydrogen phosphate dihydrate in 950 ml of demineralized water. Adjust the pH with 1 N NaOH (if pH<7.5) or with 1 N HCl (if pH>7.5). Dilute to 1 L with demineralized water using a volumetric flask. Discard the buffer solution when pH changes more than 0.05 units from the desired pH.

Beta-Glucan Substrate (0.5%)

Weigh 0.50 g (+/−0.01 g) beta-glucan from barley, medium viscosity (Supplied by Megazyme). Add 100 ml buffer solution pH 7.5. Dissolve the mixture while stirring in a water bath of about 70° C. (about 10 to 15 mins). Cool the substrate to 37° C. Suggested storage time is 1 day.

Glucose Stock Solution (1000 μg/ml)

Dissolve 0.1 g (+/−0.001 g) of anhydrous glucose with demineralized water and top up to 100 ml using a 100 ml volumetric flask.

Glucose Standard Solutions

Dilute the glucose stock solution as follow:

| | Diluted stock solution | |
| Glucose (μg/ml) | 1000 μg/ml | Demineralized water |
|---|---|---|
| 0 | 0 ml | 1 ml |
| 40 | 4 ml | Dilute to 100 ml |
| 80 | 8 ml | Dilute to 100 ml |
| 120 | 12 ml | Dilute to 100 ml |
| 160 | 16 ml | Dilute to 100 ml |

Pectinase Activity:

Dissolve 10.51 g citric acid in 950 ml of demineralized water. Adjust to pH 4.0 with NaOH 10 M. Dilute to 1 L with demineralized water using a volumetric flask. Discard the buffer solution when pH changes more than 0.05 units from the desired pH.

Poly-Galacturonic Acid Substrate 0.15%

Weigh 0.15 g (+/−0.01 g) poly-galacturonic acid—sodium salt (Sigma P-3850). Add 100 ml buffer pH 4.0 solution. Heat this solution at 80° C. with stirring for 15 minutes. Cool the substrate to 37° C. Suggested storage time is 1 day.

D (+)-Galacturonic Acid Stock Solution 1000 µg/ml

Dissolve 0.109 g (+/−0.001 g) of galacturonic acid (monohydrate) with demineralized water and top up to 100 ml using a 100 ml volumetric flask.

Galacturonic Acid Standard Solutions

Dilute the galacturonic acid stock solution as follows:

| Galacturonic acid (µg/ml) | Diluted solution 1000 µg/ml | Demineralized water |
|---|---|---|
| 0 | 0 ml | 1 ml |
| 40 | 4 ml | Dilute to 100 ml |
| 80 | 8 ml | Dilute to 100 ml |
| 120 | 12 ml | Dilute to 100 ml |
| 160 | 16 ml | Dilute to 100 ml |

Example 1

Effect on Alfalfa-Based Forage

The enzyme product KAC023-005 representing a preferred embodiment of this invention was mixed with alfalfa substrate in a dosage of 1000 g/ton. Two-hundred milligrams (200 mg) of the mixture was incubated in 100 ml syringe with 30 ml of rumen fluid which was treated with anaerobic buffer/mineral solution. Two runs of incubation were carried out, with triplicate in each run. The gas production was recorded at 12 and 24 h. Organic matter digestibility at 24 h (OMD24 h) of substrate was calculated from gas production 24 h. The results are shown in FIG. 1. Usage of enzyme in the dosage of 1000 g/T leaded to a 3.2% increase in OMD-24 h of alfalfa.

Example 2

Effect on Chinese Wildrye-Based Forage

Figure 2:
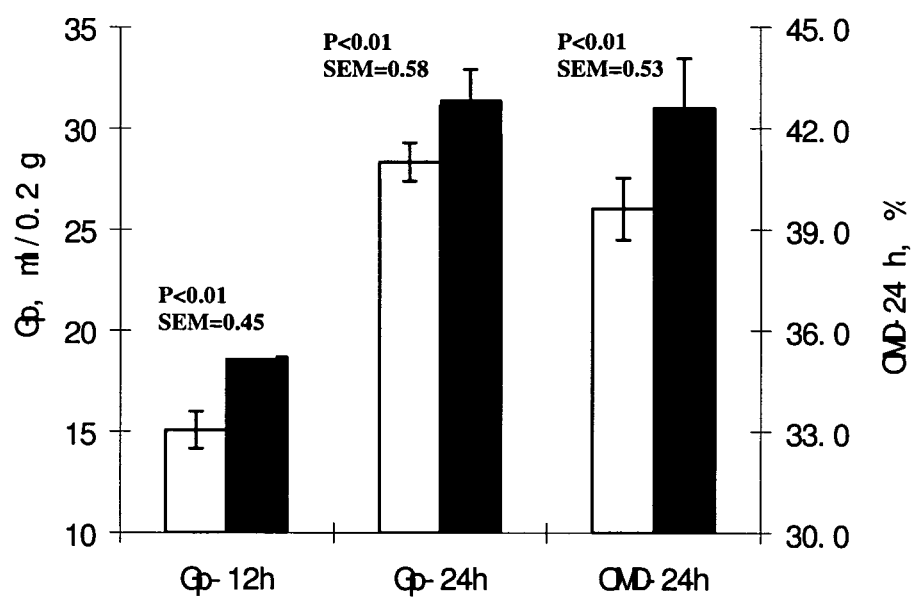
FIG. 2 is a graph of the effects of a preferred embodiment of the invention on the gas production (Gp) at 12 h and 24 h and organic matter digestibility (OMD) at 24 h in vitro of Chinese wildrye; the control (left columns) was blank with no enzyme treated; the dosage of treatment (right columns) was 1000 g/T.

KAC023-005 was mixed with Chinese wildrye substrate in a dosage of 1000 g/ton. Two-hundred milligrams (200 mg) of the mixture was incubated in a 100 ml syringe with 30 ml of rumen fluid which was treated with anaerobic buffer/mineral solution. Two runs of incubation were carried out, with triplicate in each run. The gas production was recorded at 12 and 24 h. The results are shown in FIG. 2. Supplement of enzyme enhanced the Gp-24 h and OMD-24 h of Chinese wildrye significantly by 10.9% and 7.6% respectively (p<0.01).

Example 3

Effect on Corn Silage-Based Forage

Figure 3:
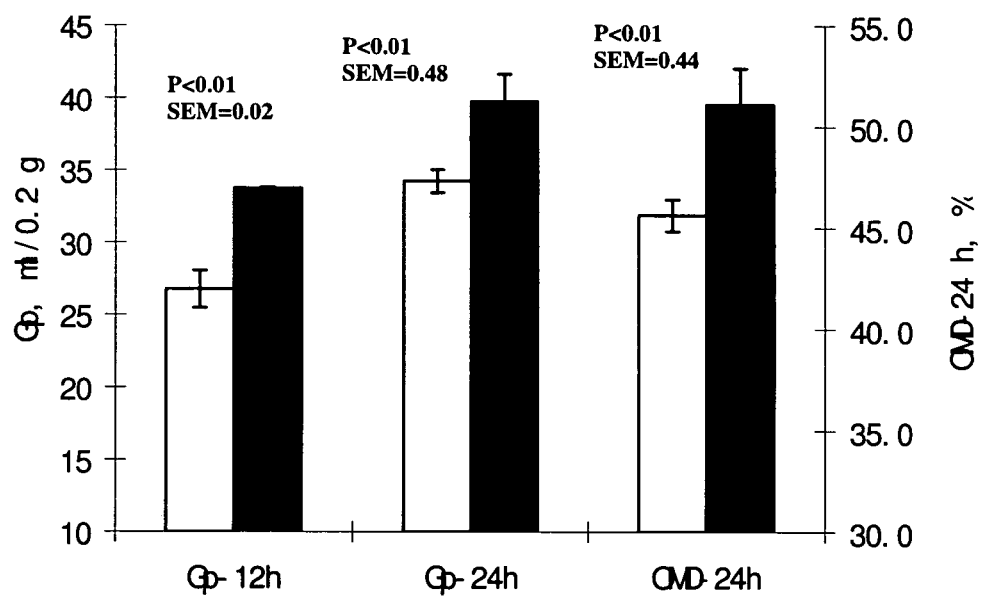
FIG. 3 is a graph of the effects of a preferred embodiment of the invention on the gas production (Gp) at 12 h and 24 h and organic matter digestibility (OMD) at 24 h in vitro of whole corn silage; the control (left columns) was blank with no enzyme treated; the dosage of treatment (right columns) was 1000 g/T.

Enzyme product KAC023-005 was mixed with corn silage-based substrate in a dosage of 1000 g/ton. Two-hundred milligrams (200 mg) of the mixture was incubated in a 100 ml syringe with 30 ml of rumen fluid which was treated with anaerobic buffer/mineral solution. Two runs of incubation were carried out, with triplicate in each run. The gas production was recorded at 12 and 24 h. The results are shown in FIG. 3. Gp-24 h and OMD-24 h of whole corn silage increased significantly (p<0.01) by 16.2% and 12.1%, respectively.

Example 4

Effect on Total Mixed Ration

Figure 4:
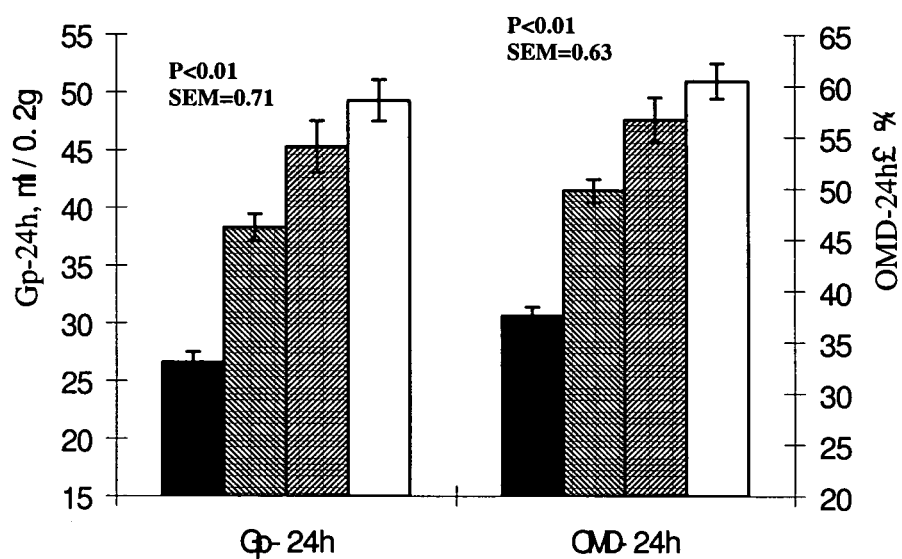
FIG. 4 is a graph of the effects of a preferred embodiment of the invention on the gas production (Gp) at 24 h and organic matter digestibility (OMD) at 24 h in vitro of imitated total mixture ration (TMR) (alfalfa:corn:soybean=50:30:20); the control (left columns) was blank with no enzyme treated; the dosages of treatment (right columns) was 500 g/T, 1000 g/T and 2000 g/T, second from left

Enzyme product KAC023-005 was mixed with a diet that simulates TMR in dosages of 500 g/ton, 1000 g/ton and 2000 g/ton. Two-hundred milligrams (200 mg) of the mixture was incubated in a 100 ml syringe with 30 ml of rumen fluid which was treated with anaerobic buffer/mineral solution. Two runs of incubation were carried out, with triplicate in each run. The gas production was recorded at 12 and 24 h. The results are shown in FIG. 4. Gp-24 h and OMD-24 h increased extremely when treated with enzymes in different dosages (p<0.01). The increased values of Gp-24 h rise with the increasing of dosage. However, the data suggest that when the enzymes were added with a dosage of 1000 g/T, the gas production may reach the plateau (p>0.05). In other words, the effects of enzymes get saturation with the dosage of 1000 g/T substrate.

Example 5

Effect on Ryegrass Neutral Detergent Fiber

Figure 5:
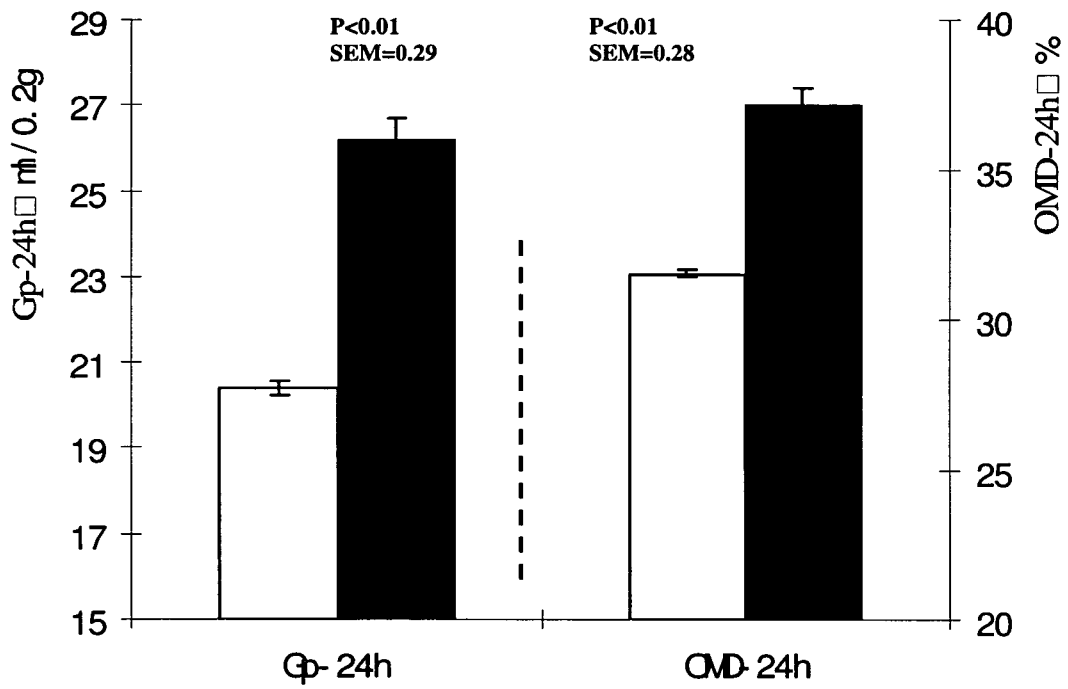
FIG. 5 is a graph of the effects of a preferred embodiment of the invention on the gas production (Gp) and organic matter digestibility at 24 h in vitro of neutral detergent fiber (NDF) extracted from ryegrass; the control (left columns) was blank with no enzyme treated; the dosage of treatment (right columns) was 1000 g/T.

Enzyme product KAC023-005 was mixed with neutral detergent fiber (NDF) substrate extracted from ryegrass in a dosage of 1000 g/ton. Two-hundred milligrams (200 mg) of the mixture was incubated in a 100 ml syringe with 30 ml of rumen fluid which was treated with anaerobic buffer/mineral solution. Two runs of incubation were carried out, with triplicate in each run. The gas production was recorded at 24 h. The results are shown in FIG. 5. Enzyme increased ryegrass NDF OMD-24 h by 18.3% (p<0.01) when incubated in vitro. This result demonstrated that the enzyme product can increase the digestibility of fiber.

Example 6

Additional TMR Test

Figure 6:
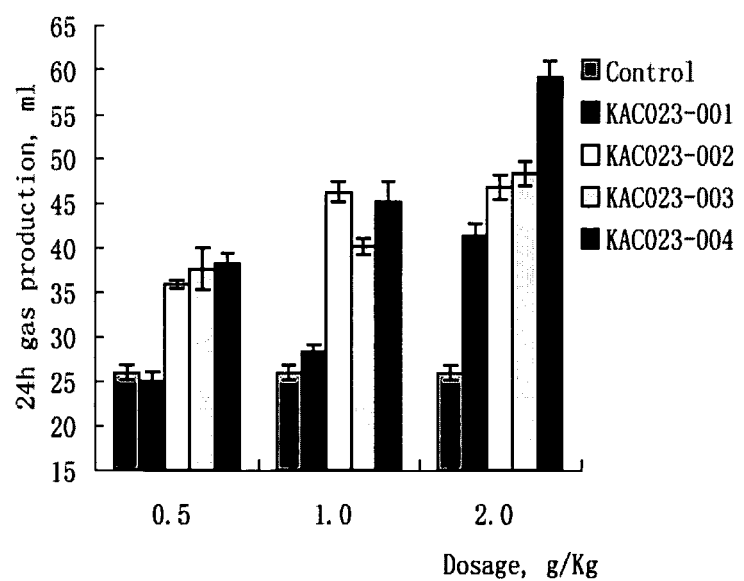
FIG. 6 is a graph of the effects of a enzyme products of the present invention on in vitro gas production at 24 h on a simulated TMR diet.

A second test was run on simulated TMR. The results of gas production at 24 h are presented in FIG. 6. Formulas KAC023-002, KAC023-003 and KAC023-4 were all effective at improving gas production. A dosage effect was also observed at the three dosages used, 0.5 g/kg, 1 g/kg and 2 g/kg. Formula KAC023-001 showed no effect at low dosage but some improvement at high dosage. Formulas KAC023-003 and KAC023-004 showed increased gas production with the increased dosages. Formula KAC023-002 reached saturation at 1 g/kg.

Figure 7:
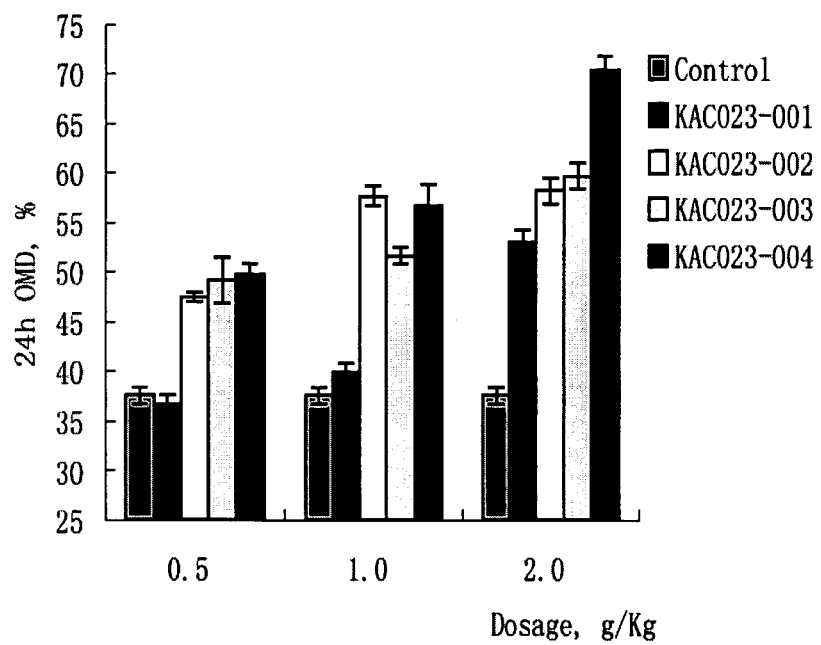
FIG. 7 presents the digestibility of the organic matter (OMD) in the simulated TMR diet of FIG. 6.

According to Menke's method, at 24 hour incubation, there is a tight correlation between gas production and digestibility. FIG. 7 presents the digestibility of the organic matter (OMD) in the simulated TMR diet. The OMD was calculated from crude protein content of substrate and Gp24 h. Because the substrate was the same for all the four enzyme formulas, the effects of enzymes on OMD showed a similar pattern to Gp24 h. Taken together the results from gas production and digestibility, all of the four enzymes formulas could increase the digestibility of simulated TMR when incubated in vitro. Among these four formulas, KAC023-001 was the least effective. It showed effect only at high dosage (2 g/Kg). KAC023-002, KAC023-003 and KAC023-004 were all statistically better than KAC023-001. There was no statistical difference between KAC023-002 and KAC023-003. Among all of the four samples, KAC023-004 was the best. Consequently, new formulas in the next experiment were designed based on KAC023-004.

Cellulase and xylanase were considered to be the most important exogenous enzymes in dairy culture (Beauchemin et al., 2003a, Beauchemin et al., 2003b, Beauchemin et al., 2003c). KAC023-001 contains only cellulase and xylanase. The data above indicated that when the levels of cellulase and xylanase were low, there was no effect on the in vitro digestibility of TMR. At high dosage (2 g/kg) KAC023-001 showed statistical effect. This suggests that the levels of these two enzymes need to be increased by further optimization.

In addition to cellulase and xylanase, other enzymes also play important roles. All four formulas contained the same levels of cellulase and xylanase. Compared to KAC023-001, KAC023-002, KAC023-003 and KAC023-004 contained additional β-glucanase, pectinase and both, respectively. This suggests that supplementing β-glucanase and/or pectinase is essential for the effectiveness. Shortage of these two enzymes in the rumen may be the limiting factors for the digestibility of organic matter. β-glucan is a major component in the bran of grasses. It consists of linear unbranched polysaccharides of linked β-(1,3)- and β-(1,4)-D-glucopyranose units. Pectin is a heterogeneous grouping of acidic structural polysaccharides, found in peel of fruits and vegetables. The majority of the structure consists of homopolymeric partially methylated poly-α-(1,4)-D-galacturonic acid residues. Both β-glucan and pectin form steric hindrance for the release of nutrients in feed. Therefore, if β-glucan and pectin are not effectively broken down, the digestibility of organic matter can be affected. Our data clearly showed that addition of either β-glucanase or pectinase significantly improved the efficiency of the supplemented enzymes. Addition of both enzymes exerted the best efficiency.

Example 7

Additional Test on NDF

Figure 8:
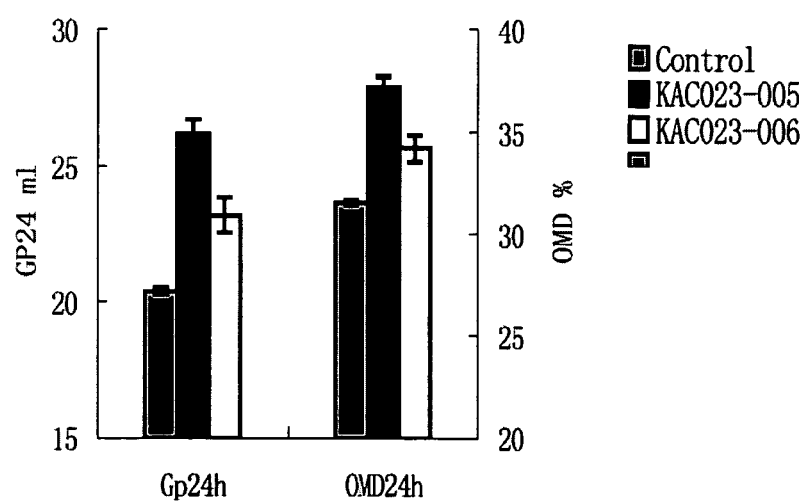
FIG. 8 is a graph of the effects of enzyme products of the present invention on in vitro fiber digestibility at 24 h on ryegrass NDF.

In order to better evaluate the enzyme performance in fiber digestion, we used purified ryegrass NDF as substrate. There was no protein or starch in pure NDF, so the interference of these two factors can be eliminated. We also made modifications on our enzyme formulas based on the results from the first round. Both KAC023-005 and KAC023-006 have higher level of cellulase and xylanase. In addition, both formulas contain β-glucananse, pectinase, β-mannanase and α-galactosidase. The dosage used is 1 g/kg. The results of Gp and OMD of ryegrass NDF are shown in FIG. 8. Both two formulas increased the Gp and digestibility of fiber significantly ($p<0.01$) when incubated in vitro. This suggests that both enzyme formulas can increase the digestibility of fiber.

Compared to KAC023-006, KAC023-005 is more effective. Adding 1.0 g/Kg Sample 1 to ryegrass NDF resulted an 18.3% increase on digestibility. Except for cellulase, all the other enzymes activities in these two formulas were the same. The activity of cellulase in KAC023-005 was lower than that in KAC023-006, but the overall efficiency is better for KAC023-005. This suggests that higher enzyme activities does not necessarily mean better efficiency. Instead, an optimal combination of different enzymes contributes more to the overall digestibility. This result is contradictory to previous research conducted by Eun and Beauchemin (in press). Eun and Beauchemin used several commercial enzyme products to study the cellulase activity and in vitro gas production, and found a linear correlation between these two parameters ($r=0.71$; $p<0.01$). One explanation is that in Eun's paper the cellulase activity actually referred to endoglucanase activity instead of the overall cellulase activity, while in our research we measured the overall cellulase activity. Thus, linear correlation between endoglucanase and gas production may not equal to a linear correlation between overall cellulase activity and gas production. Another possible explanation is that the conditions and methods by which cellulase activity was measured were very different in these two researches. The third possibility is that the linear correlation reported in Eun's paper is substrate-specific. In Eun's paper alfalfa was used as substrate, while in our study TMR was used.

Example 8

Stability of Enzyme in Rumen

Figure 9:
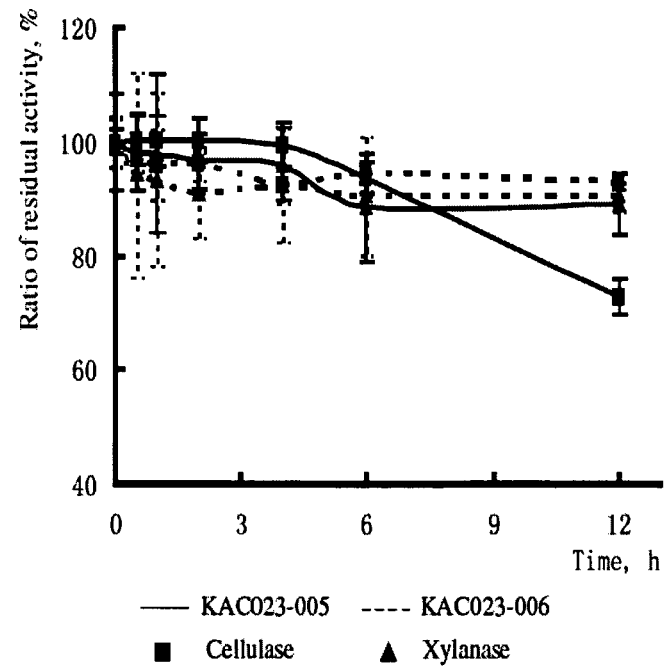
FIG. 9 is a graph of the stability of cellulase and xylanase in the presence of ruminal fluid.

One of the major concerns of using enzyme additives in rumen is the stability of these enzymes. Ruminal microbes secrete protease which may quickly degrade exogenous enzymes. In this study, the stability of cellulase and xylanase in both formulas was determined in vitro. We used high dosage (100 kg/T) in order to minimize the noise from endogenous activities of cellulase and xylanase so that the endogenous activities of these two enzymes are negligible compared to the exogenous enzymes. Therefore, in our study, we did not need to worry about the interference from the endogenous enzymes. The stability of our cellulase and xylanase is shown in FIG. 9. The cellulase activity in KAC023-005 remained 72.9% after 12 h of incubation, and all the other enzyme activities in both samples remained over 90%.

Example 10

Gas Production Using Various Enzyme Products

A series of experiments were conducted to understand better the role of individual enzymes, the amounts of individual enzymes and the ratio of enzymes on the efficacy of the enzyme products.

Initially, four different enzyme products based on KAC023-5 were formulated and evaluated using the gas production method under ruminal conditions. The dosage used was 1.0 g/Kg.

TABLE 5

| | Enzyme Products | | | | |
|---|---|---|---|---|---|
| | KAC023-11 | KAC023-12 | KAC023-13 | KAC023-14 | KAC023-15 |
| Cellulase | 500 | 500 | 1,000 | 1,000 | 900+100 |
| Xylanase | 3,000 | 3,000 | 1,500 | 1,500 | 1,500 |
| β-Glucanase | 400 | 400 | 400 | 400 | 400 |
| Pectinase | 2 | 2 | 2 | 2 | 2 |
| β-Mannanase | 200 | 200 | 200 | 200 | 200 |
| α-Galactosidase | Present | Present | Present | Present | Present |

TABLE 6

| Gas production on enzyme products of Table 9 | | | | |
|---|---|---|---|---|
| | Alfalfa | Chinese wildrye | Corn stover | Corn silage |
| KAC023-11 | 31.2 | 27.1 | $27.1^{ab}$ | 32.0 |
| KAC023-12 | 29.6 | 27.1 | $27.0^{ab}$ | 32.4 |
| KAC023-13 | 29.7 | 25.6 | $25.4^{c}$ | 32.3 |
| KAC023-14 | 28.1 | 26.2 | $27.7^{a}$ | 33.5 |

TABLE 6-continued

Gas production on enzyme products of Table 9

|  | Alfalfa | Chinese wildrye | Corn stover | Corn silage |
|---|---|---|---|---|
| KAC023-15 | 30.5 | 27.3 | 25.8$^{bc}$ | 32.3 |
| Control | 30.8 | 27.3 | 26.7$^{abc}$ | 33.5 |
| S.E.M | 1.23 | 0.80 | 0.46 | 0.75 |

$^{a,b,c}$Different letters within a column differ (p < 0.05)

None of these formulas in Table 5 was effective, suggesting that in addition to the composition of enzyme profile, the ratio of different enzymes is also important.

One of the previous formulations were evaluated against each other under rumen conditions; dosage used was 1.0 g/Kg.

TABLE 7

| | Enzyme Products | | | | |
|---|---|---|---|---|---|
| | KAC023-05 | KAC023-16 | KAC023-17 | KAC023-18 | KAC023-19 |
| Cellulase | 400 | 400 | 400 | 400 | 800 |
| Xylanase | 1500 | 1500 | 1500 | 1500 | 3000 |
| β-Glucanase | 450 | 450 | 450 | 450 | 900 |
| Pectinase | 0 | 2 | 0 | 0 | 0 |
| β-Mannanase | 200 | 200 | 200 | 200 | 200 |
| α-Galactase | present | 0.0 | 0.0 | present | 0.0 |

TABLE 8

Gas Production of the enzyme products of Table 7

|  | Alfalfa | Chinese wildrye | Corn stover | Corn silage |
|---|---|---|---|---|
| KAC023-05 | 29.5$^{ab}$ | 29.0$^a$ | 26.2$^{ab}$ | 34.6$^b$ |
| KAC023-16 | 30.1$^a$ | 29.3$^a$ | 27.1$^a$ | 34.4$^b$ |
| KAC023-17 | 31.3$^a$ | 29.4$^a$ | 27.2$^a$ | 34.3$^b$ |
| KAC023-18 | 30.9$^a$ | 29.3$^a$ | 27.6$^a$ | 36.5$^a$ |
| KAC023-19 | 30.5$^a$ | 28.5$^{ab}$ | 26.4$^{ab}$ | 36.0$^a$ |
| Control | 28.4$^b$ | 28.0$^b$ | 25.8$^b$ | 32.8$^c$ |
| S.E.M | 0.55 | 0.40 | 0.44 | 0.69 |

$^{a,b}$Different letters within a column differ (p < 0.05)

The results suggest that the ratio of cellulase and xylanase is important. If xylanase is too high (KAC23-11 and KAC023-12) or if cellulase is too high (KAC023-13, KAC023-14 and KAC023-15), the enzyme product lost efficiency. By comparing KAC023-17 and KAC023-18, alpha-galactosidase seemed to provide certain improvement for corn silage. By comparing KAC023-05 and KAC023-19, the enzyme activities in KAC023-05 already reached saturation. Further increase in cellulase, xylanase and beta-glucanase did not provide further efficiency.

The importance of pectinase and alpha-galactosidase were next evaluated under rumen conditions; dosage used was 1.0 g/Kg.

TABLE 9

| | Enzyme Products | | | |
|---|---|---|---|---|
| | KAC023-20 | KAC023-21 | KAC023-18 | KAC023-22 |
| Cellulase | 400 | 400 | 400 | 400 |
| Xylanase | 1500 | 1500 | 1500 | 1500 |

TABLE 9-continued

| | Enzyme Products | | | |
|---|---|---|---|---|
| | KAC023-20 | KAC023-21 | KAC023-18 | KAC023-22 |
| β-Glucanase | 450 | 450 | 450 | 450 |
| Pectinase | 2 | 2 | 0 | 0 |
| β-Mannanase | 200 | 200 | 200 | 200 |
| α-Galactosidase | present | 0 | present | 0 |

TABLE 10

Gas production results of the products of Table 9

|  | Alfalfa | Chinese wildrye | Corn stover | Corn silage | TMR |
|---|---|---|---|---|---|
| KAC023-20 | 37.1$^a$ | 29.7$^a$ | 25.8$^a$ | 35.9$^a$ | 48.7$^a$ |
| KAC023-21 | 27.9$^b$ | 29.7$^a$ | 25.8$^a$ | 35.1$^{ab}$ | 48.5$^a$ |
| KAC023-18 | 25.5$^b$ | 27.7$^b$ | 25.0$^{ab}$ | 33.9$^{abc}$ | 47.0$^{ab}$ |
| KAC023-22 | 25.4$^b$ | 26.8$^c$ | 23.8$^b$ | 32.4$^{bc}$ | 45.9$^b$ |
| Control | 21.5$^c$ | 24.9$^d$ | 23.4$^b$ | 31.4$^c$ | 44.1$^c$ |
| S.E.M | 0.82 | 0.61 | 0.51 | 0.78 | 0.47 |

$^{a,b,c,d}$Different letters within a column differ (p < 0.05)

By comparing KAC023-18 and KAC023-22, and KAC023-20 and KAC023-21, it is clear that the alpha-galactosidase is needed. By comparing KAC023-18 and KAC023-20, and KAC023-22 and KAC023-21, it is clear that pectinase is needed.

An experiment was run to further confirm the importance of each component enzyme by comparing under rumen conditions KAC023-20 against enzyme products with each on of the individual component enzymes removed; dosage was 1.0 g/Kg.

TABLE 11

| | Enzyme Products | | | | | | |
|---|---|---|---|---|---|---|---|
| | KAC023-20 | B | C | D | E | F | G |
| Cellulase | 400 | — | 400 | 400 | 400 | 400 | 400 |
| Xylanase | 1500 | 1500 | — | 1500 | 1500 | 1500 | 1500 |
| Glucanase | 450 | 450 | 450 | — | 450 | 450 | 450 |
| Pectinase* | 2 | 2 | 2 | 2 | — | 2 | 2 |
| Mannanase | 200 | 200 | 200 | 200 | 200 | — | 200 |
| Galactase | present | present | present | present | present | present | — |

TABLE 12

Gas production of the enzyme products of Table 10

|  | Alfalfa | Chinese wildrye | Corn stover | Corn silage |
|---|---|---|---|---|
| KAC023-20 | 28.4$^a$ | 29.6$^a$ | 29.1$^a$ | 38.6$^a$ |
| B | 25.9$^{bc}$ | 26.3$^c$ | 25.5$^c$ | 34.1$^{bc}$ |
| C | 26.1$^{bc}$ | 27.5$^c$ | 27.4$^{bc}$ | 34.9$^{bc}$ |
| D | 27.8$^b$ | 27.8$^{bc}$ | 27.6$^{bc}$ | 34.5$^{bc}$ |
| E | 24.6$^c$ | 27.8$^{bc}$ | 26.7$^{cd}$ | 34.9$^{bc}$ |
| F | 24.9$^{bc}$ | 29.5$^a$ | 27.1$^{bc}$ | 36.6$^{bc}$ |
| G | 23.9$^c$ | 29.2$^{ab}$ | 27.4$^{bc}$ | 37.4$^{ab}$ |
| Control | 22.1$^d$ | 25.9$^c$ | 25.1$^c$ | 32.9$^c$ |
| S.E.M | 0.56 | 0.49 | 0.38 | 0.52 |

$^{a,b,c,d}$Different letters within a column differ (p < 0.05)

The results indicate that all of the enzymatic activities of the six component enzymes are important for the best performance. Omission of any of the enzymatic activities resulted in statistically significant reduction in gas production.

Example 11

Materials and Methods

Enzyme Sample

The enzyme sample used in this Example is formula KAC023-20 as described in Table

TABLE 13

| Enzyme Product | |
|---|---|
| | KAC023-20 |
| Cellulase | 400 |
| Xylanase | 1500 |
| β-Glucanase | 450 |
| Pectinase | 2 |
| β-Mannanase | 200 |
| α-Galactosidase | present |

Trial Animals

Balanced within parity, by days in milk (DIM) and lactation performance, forty lactating Chinese Holstein were chosen from a dairy farm in Nanjing, Jiangsu Province and randomly assigned into four groups: Control and Treatments 1-3, with ten animals for each group. In the Treatments 1, 2, and 3, KAC023-20 was added into feed concentrates at 250 g/T, 500 g/T, and 1000 g/T, respectively. The details of trial animals and grouping are provided in Table 14.

TABLE 14

| Experimental design and information of trial animals | | | | |
|---|---|---|---|---|
| | Control | Treatment 1 | Treatment 2 | Treatment 3 |
| No. of animals | 10 | 10 | 10 | 10 |
| Dosage, g/T concentrate | 0 | 250 | 500 | 1000 |
| Parity | 2.4 | 2.5 | 2.4 | 2.4 |
| DIM | 147.1 | 146.8 | 146.5 | 147.2 |
| Milk yield, Kg/d | 28.95 | 28.90 | 28.90 | 28.90 |
| Milk fat, % | 3.406 | 3.402 | 3.401 | 3.401 |
| Milk protein, % | 2.922 | 2.941 | 2.922 | 2.900 |

The composition of concentrate is presented in Table 15.

TABLE 15

| Composition of concentrates | | | | |
|---|---|---|---|---|
| | Control, % | Treatment 1, % | Treatment 2, % | Treatment 3, % |
| Corn | 47.0 | 47.0 | 47.0 | 47.0 |
| Wheat bran | 13.3 | 13.3 | 13.3 | 13.3 |
| DDGS | 5.0 | 5.0 | 5.0 | 5.0 |
| Soy bean meal | 13.5 | 13.5 | 13.5 | 13.5 |
| Cottonseed meal | 14.0 | 14.0 | 14.0 | 14.0 |
| Calcium carbonate | 2.0 | 2.0 | 2.0 | 2.0 |
| Calcium bicarbonate | 1.6 | 1.6 | 1.6 | 1.6 |
| Sodium chloride | 1.0 | 1.0 | 1.0 | 1.0 |
| Sodium bicarbonate | 1.5 | 1.5 | 1.5 | 1.5 |
| Premix, 1% | 1.0 | 1.0 | 1.0 | 1.0 |

TABLE 15-continued

| Composition of concentrates | | | | |
|---|---|---|---|---|
| | Control, % | Treatment 1, % | Treatment 2, % | Treatment 3, % |
| Enzyme Sample, (g/t) | 0.0 | 0.025 | 0.05 | 0.1 |
| Rice bran | 0.1 | 0.075 | 0.05 | 0.0 |
| Total | 100.0 | 100.0 | 100.0 | 100.0 |

Concentrate was mixed with silage and forage in 1:1 ratio to make complete diet as a TMR. The intake of TMR was based on the lactation phase of dairy cows. The composition and intake of TMR per animal per day are presented in Table 16. Trial animals were fed with TMR three times per day. Fresh water was available at all time with no restriction

TABLE 16

| Composition of TMR and intake per animal per day | |
|---|---|
| Components | Weight (Fresh), Kg |
| Concentrate | 10.9 |
| Corn silage | 15.0 |
| Beet pulp pellets | 2.0 |
| Alfalfa | 2.0 |
| Chinese wildrye | 2.0 |
| Brewers grains, wet | 10.0 |
| Apple pomace | 1.0 |
| Total | 42.9 |

The study was conducted in one-way experiment of 45 days composed of 15 d adjustment period and 30 d testing period.

Parameters Measured

All the parameters, including milk yield, milk fat, milk protein, lactose, NFS and SCC were determined at the beginning and end of the adjustment period.

In the testing period, milk yield was recorded daily. Milk was sampled every 2 days to determine the content of milk fat, milk protein, lactose and NFS. Milk samples were obtained on every Wednesday to measure SCC.

Data Analysis

The data were analyzed by One-way ANOVA using the statistical software SAS (v 6.12, 1996). Means are different when $p<0.05$ and significantly difference when $p<0.01$.

Results

Effects of Enzyme Sample on Milk Yield

Figure 10:
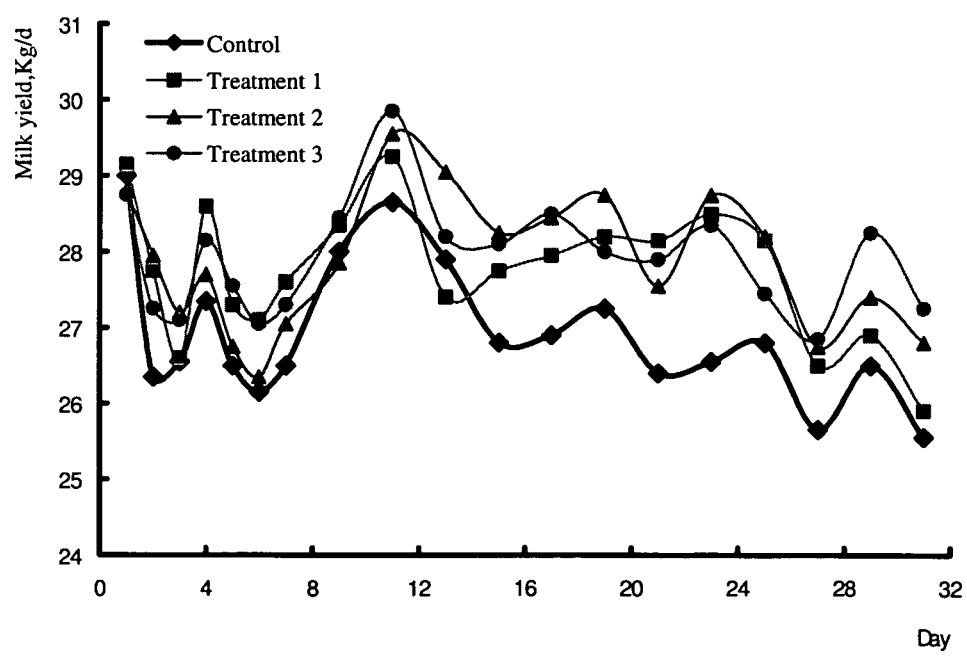
FIG. 10 is a chart of the trend of milk yield during the testing period.

The lactation curve during the whole testing period is presented in FIG. 10. As the trial was carried out after the peak lactation phase, there is an overall pattern of declination in milk yield with some degree of fluctuation. Milk yield of all the 3 treatments were higher than that of the Control. In the first ten days, this trend was not very apparent. However, the difference between the treatments and Control became increasingly apparent when the treatment was prolonged. The declination in milk yield was significantly slowed down.

Statistical analysis on milk yield is summarized in Table 20. The data of every 6 days was grouped into one lactating stage and analyzed by statistics. The results were consistent with the curve in FIG. 10. There was no statistical difference in the first two stages (00-12 d) ($p>0.05$). Starting from the third stage, the positive effect of KAC023-20 on milk yield was achieved as it significantly enhanced milk yield (p<0.01). Except for the third stage (13-18 d) (p<0.05), KAC023-20 showed no effect on the milk yield at all dosages (p>0.05), suggesting that exogenous enzyme activities were already saturated with KAC023-20 at 250 g/T.

KAC023-20 showed no effect in the first two stages (00-12 d), implying that the dairy cows may need a long time (over 22 days) to adapt to the exogenous enzymes. Nevertheless, the data of the overall testing period (00-30 d) showed a significant increase in milk yield (p<0.01) (Table 17). On the average, application of KAC023-20 increased daily milk yield by 3.2% or 0.85 Kg/head.

TABLE 17

Effects of KAC023-20 on milk yield, Kg/d

| | Control | Treatment 1 | Treatment 2 | Treatment 3 | S.E.M. | P |
|---|---|---|---|---|---|---|
| 00-06 d | 26.90 ± 0.49 | 27.49 ± 0.68 | 27.17 ± 0.59 | 27.40 ± 0.41 | 0.225 | 0.2778 |
| 07-12 d | 28.18 ± 0.41 | 28.33 ± 0.93 | 28.82 ± 0.87 | 28.83 ± 0.89 | 0.517 | 0.6825 |
| 13-18 d | $26.98 \pm 0.24^{Cb}$ | $27.97 \pm 0.23^{Ba}$ | $28.48 \pm 0.25^{Aa}$ | $28.20 \pm 0.26^{ABa}$ | 0.141 | 0.0004 |
| 19-24 d | $26.58 \pm 0.20^{Bb}$ | $28.27 \pm 0.20^{Aa}$ | $28.17 \pm 0.60^{Aa}$ | $27.90 \pm 0.45^{Aa}$ | 0.232 | 0.0030 |
| 25-30 d | $25.70 \pm 0.18^{Bb}$ | $26.63 \pm 0.23^{Aab}$ | $26.98 \pm 0.36^{Aa}$ | $27.45 \pm 0.72^{Aa}$ | 0.248 | 0.0062 |
| 00-30 d | $26.91 \pm 0.92^{Bb}$ | $27.74 \pm 0.89^{Aa}$ | $27.73 \pm 1.08^{Aa}$ | $27.86 \pm 0.82^{Aa}$ | 0.101 | 0.0005 |

$a,b$ Means with the different letters within a row differ significantly (p < 0.07)
$A,B,C$ Means with the different letters within a row differ (p < 0.05)

Effects of KAC023-20 on Milk Components

Figure 11:
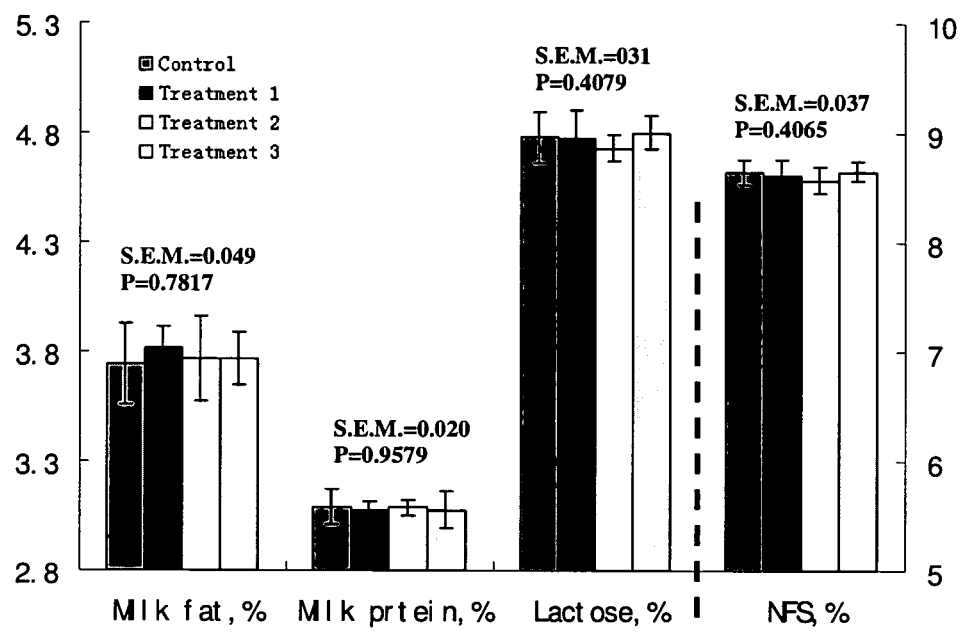
FIG. 11 is a chart of the effects of Enzyme Sample on milk components.

KAC023-20 showed no effect on the milk components in this study, as presented in FIG. 11. No significant increase on milk fat was observed in the 3 treatments. At the dosage of 250 g/T, there was a numerical improvement by approximate 2.7% compared with Control (p=0.3023).

There was no significant difference obtained on milk protein, lactose or NFS between the treatments and Control (p>0.05).

Effect of KAC023-20 on Somatic Cell Count (SCC)

Figure 12:
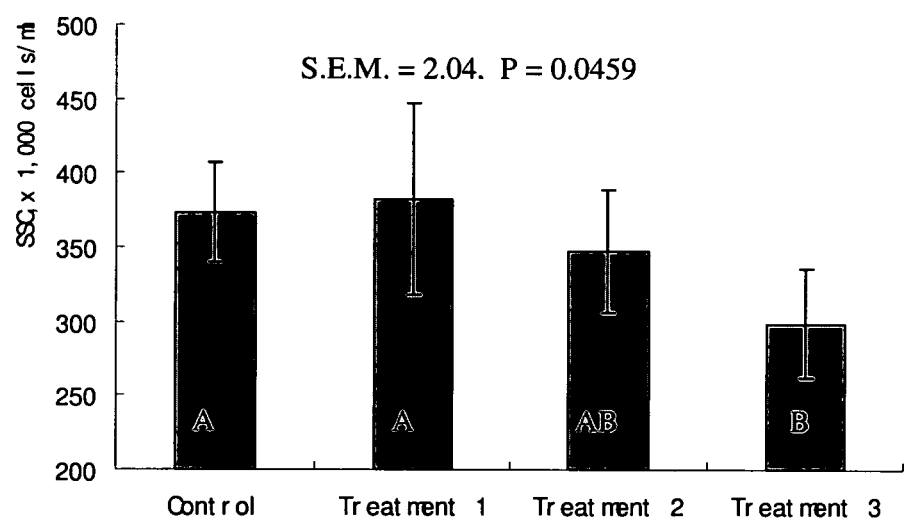
FIG. 12 is a chart of the effects of Enzyme Sample on SCC (means with the different letter within the column differ (P<0.05)).

SCC determined from milk is an important and most widely accepted criterion to reflect the health condition of dairy cows. High level of SCC is usually an indicator of poor health condition, such as subclinical mastitis, ketosis etc. The effect of KAC023-20 on SCC is illustrated in FIG. 12.

No positive effect was found at low dose of KAC023-20 (250 g/T). Numerical reduction in SCC was observed at intermediate application rate (500 g/T), and significant reduction was observed at high application rate (1000 g/T) (p<0.05). This suggests that KAC023-20 enhanced the health condition of lactating dairy cows.

Discussion

In the dairy cow feeding industry, energy becomes the bottleneck of animal productivity including milk production, reproduction and health maintenance. Insufficient energy supply would shorten peak lactation phase and drop the overall milk yield. Improving fiber digestibility can enhance energy release, and thus provide better energy to the animals to exert productivity. Crude fiber in normal feedstuff consists of linear unbranched polysaccharides of linked β-(1,3)- and β-(1,4)-D-glucopyranose units. These units can fold and condense into crystalline and non-crystalline regions. The fibrolytic enzymes excreted by bacteria in rumen can degrade the non-crystalline region of fiber, but to date, there is no evidence to demonstrate that the bacterial enzymes can degrade the crystalline region. In rumen, the crystalline region can only be degraded by the exoglucanase and avicelase excreted by the rumen fungi. Since the ruminal microflora is dominated by bacteria, so the hydrolysis of fiber becomes limited by the two fungal enzymes exoglucanase and avicelase. Exogenous enzymes have been shown to improve fiber digestion by either directly degrade the crystalline regions of fiber into cellobiose and glucose, or to increase the rumen bacteria population. Nsereko et al. (2002) found that the quantity of bacteria competent in degrading cellobiose and xylan increased significantly when fibrolytic enzymes were supplemented in diets (p<0.05). Effective hydrolysis of fiber by exogenous enzymes has been previously observed by Lewis et al. (1996), who showed that exogenous xylanase and cellulase significantly increased the digestibility of DM, NDF and ADF. This study clearly demonstrates that effective fiber hydrolysis through supplementation of Enzyme Sample to diet can significantly increase milk yield (p<0.01) and numerically increased milk fat (p>0.05) of dairy cows in the mid-lactation phase, confirming the positive correlation between energy availability and milk yield.

In China, there is a trend in increasing the ratio of concentrate to roughage in pursuit of higher milk yield. The consequence of high level of concentrate in the rumen is higher concentration of lactic acids, leading to lower rumen pH. As cellulolytic bacteria in the rumen are extremely sensitive to acidic conditions, ruminal pH below 6.0 to 6.2 has been considered detrimental to the growth of these bacteria (Russell and Wilson, 1996). Deviation of the optimal pH of 6.2 for fibrolytic bacteria in the rumen will certainly result in a series of metabolic diseases, i.e. acidosis and ketosis. Therefore high level of concentrate will seriously impair the function of fibrolytic bacteria and compromise the digestibility of fiber. Supplementing ruminant diets with exogenous enzymes take advantage of the lower pH optima of these enzymes, usually between 4.0 and 6.0, and hence highly suitable for rumen acidified by high level of concentrates.

Somatic cell count is widely used as indicator of health of cows, which is critical to milk production. Optimal milk production can only be achieved when SCC is below the threshold of 71,000 cells/ml, and each doubling of SCC above the threshold will lead to additional milk loss of 1.5 lb/day (Shook and Saeman, 1983). In this study, we found that SCC was only decreased by treatment with KAC023-20 at 1000 g/T (p<0.05), but not at other dosages. This strongly suggests a dose-dependant relationship between enzyme combinations of the present invention and the immune system or health of dairy cows. Since KAC023-20 improved energy release from feed, it is not surprising that better energy balance led to healthier cows. Our result is also consistent with a previous report by Yang et al. (1999), which showed a similar dose-dependant increase in milk yield from 23.7 to 24.6 and 25.6 Kg/d, by exogenous enzymes at 1000 to 2000 g/T respectively.

Conclusions

In summary, supplementation with KAC023-20 enhanced the lactation performance without affecting milk components in this study. This study shows that KAC023-20 at 250, 500, and 1000 g/T significantly increased milk yield, although the application dosage of 250 g/T may be the most cost effective in enhancing lactation performance. SCC was decreased at the dosage of 1000 g/T, which indicated that KAC023-20 improved the health condition of dairy cows when supplemented at a high level.

Example 12

Materials and Methods

Enzyme Sample

The Enzyme Sample used in this trial is formula KAC023-20 as described in Example 11.

Trial Animals

Based on the parity, Days in Milk (DIM) and lactation performance, 72 lactating Chinese Holstein cows were chosen from a dairy farm in Shenyang City, Liaoning Province, paired and divided into 2 groups, namely Control and Treatment with 36 animals each. In the treatment, Enzyme Sample was added into concentrate at 500 g/Ton of concentrate. The details of trial animals and grouping were given in Table 18.

TABLE 18

Experimental design and information of trial animals

|  | Control | Treatment |
|---|---|---|
| No. of animals | 36 | 36 |
| Dosage, g/T concentrate | 0 | 500 |
| Parity | 2.6 | 2.4 |
| DIM | 151 | 161 |
| Milk yield, Kg/d | 31.23 | 31.14 |
| Milk fat, % | 2.51 | 2.55 |
| Milk protein, % | 3.34 | 3.28 |
| SCC, ×1000/ml | 124 | 117 |

The components of concentrate are presented in Table 19.

TABLE 19

Components of concentrate

|  | Control, % wt | Treatment, % wt |
|---|---|---|
| Corn | 49.0 | 49.0 |
| Wheat bran | 14.8 | 14.8 |
| DDGS | 5.0 | 5.0 |
| Soy bean meal | 11.5 | 11.5 |
| Cottonseed meal | 6.0 | 6.0 |
| Peanut meal | 6.9 | 6.9 |
| Calcium carbonate | 2.0 | 2.0 |
| Calcium bicarbonate | 1.7 | 1.7 |
| Sodium chloride | 1.0 | 1.0 |
| Sodium bicarbonate | 1.5 | 1.5 |
| Premix, 1% | 1.0 | 1.0 |
| Enzyme Sample | 0.0 | 0.05 |
| Rice bran | 0.05 | 0.0 |
| Total | 100.0 | 100.0 |

Concentrate was mixed with silage and forage into a completed diet as a total mixed ration (TMR). The intake of TMR was based on the lactation phase of dairy cows. The components and intake of TMR per animal per day were presented in Table 20. Trial animals were fed three times per day and fresh water was available at all times.

TABLE 20

Components of TMR and intake per animal per day

| Components | Weight (Fresh), Kg |
|---|---|
| Concentrate | 10.0 |
| Corn silage | 17.0 |
| Alfalfa | 1.4 |
| Chinese wildrye | 3.2 |
| Brewers grains, wet | 6.0 |
| Corn straw | 1 |
| Total | 38.8 |

The study was conducted in Paired-Samples experiment with 55 days composed of 15 d pretreatment period and 40 d testing period.

Parameter Determined

All the parameters, such as milk yield, milk fat, milk protein, and SCC were determined at the beginning and end of the pretreatment period.

In the testing period, milk yield was recorded every 5 days. Milk was sampled every 15 days to determine the contents of milk fat, milk protein, and SCC.

Data Analysis

The data were analyzed by Paired-Samples T-test using the statistical software SAS (v 6.12, 1996), therefore the error bars are not included in data analysis. Means are different when $p<0.05$ and significantly difference when $p<0.01$.

Results and Discussions

Effects of Enzyme Sample on Milk Yield

Figure 13:
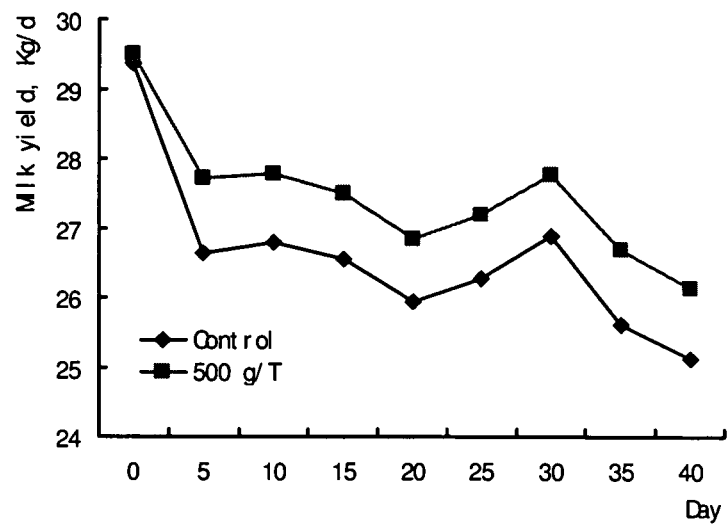
FIG. 13 is a chart of the trend of milk yield in Example 12.

The lactation curve in whole testing period was described in FIG. 13. Milk yield of the Treatment group was higher than the Control and the declination in milk curve was significantly slowed down by Enzyme Sample treatment.

Figure 14:
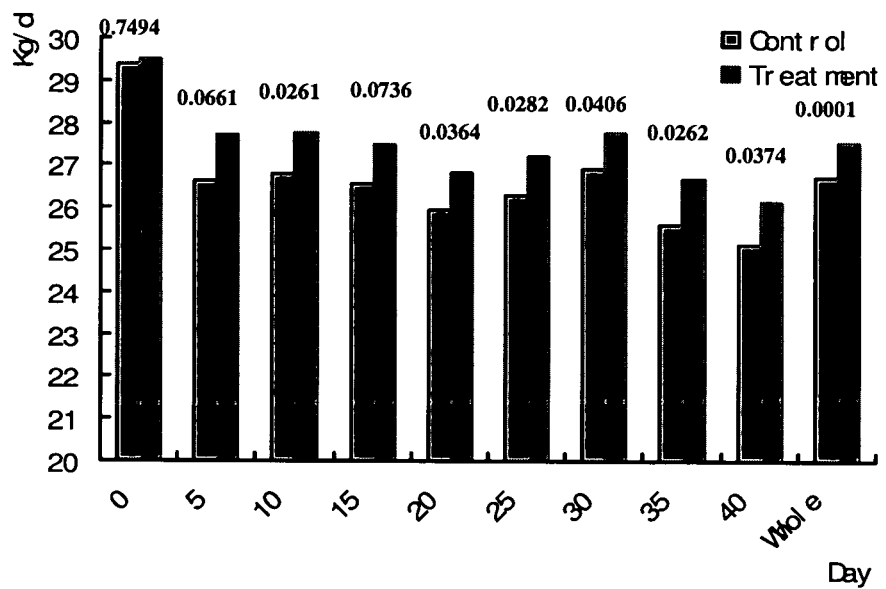
FIG. 14 is a chart of the effects of Enzyme Sample on milk yield, Kg/d (P values are presented in the figure).

Statistical results on milk yield were given in FIG. 14. The data of every 5 days were collected to be as a lactating stage and statistical analysis was conducted. The results were consistent with the milk curve. There was no stable statistical difference observed in the first four stages (00-20 d). From the fifth stage, the positive statistical effect of Enzyme Sample on milk yield was obtained. Enzyme Sample enhanced the milk yield ($p<0.05$). For the entire testing period, the milk yield of Treatment group was significantly higher than the Control ($p<0.01$).

No effect in the first four stages (00-20 d) implies that the dairy cows might need a long time to adapt to exogenous enzymes. From the whole testing period, utilization of Enzyme Sample can increase the milk yield by 0.82 Kg/d per head or 3.05% approximately.

Effects of Enzyme Sample on Milk Components

Figure 15:
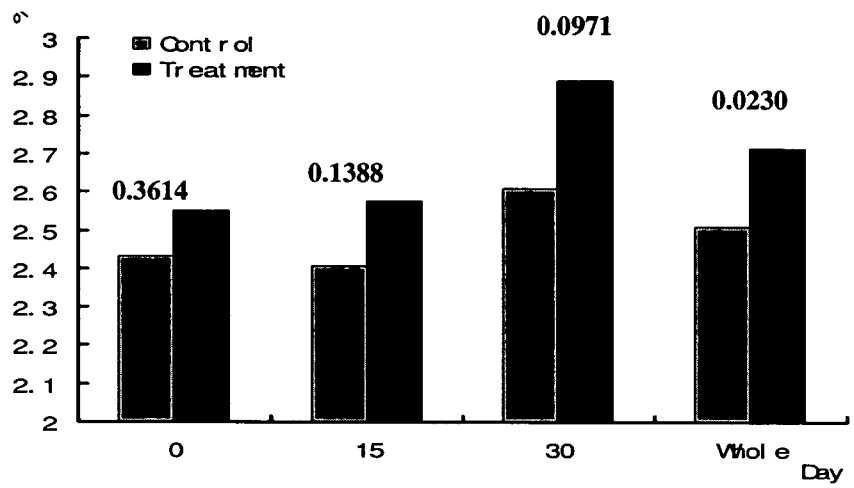
FIG. 15 is a chart of the effects of Enzyme Sample on milk fat (P values are presented in the figure).

Effect of Enzyme Sample on milk fat was presented in FIG. 15. No statistical increase on milk fat was observed in different stages in the testing period when supplemented with Enzyme Sample ($p>0.05$). However, for the entire testing period, a significant increase was obtained in Treatment (p<0.05), which suggested that Enzyme Sample had a positive effect on milk fat content.

In a former animal trial conducted in Nanjing (Example 11), Enzyme Sample showed only numerical but no statistical increase on milk fat, which is different from the results of this trial. One reason might be that the milk fat content in this trial (2.5%) was lower than that of Nanjing farm (3.2%) at the beginning of the animal trials. Lower milk fat is generally easier to be increased.

Figure 16:
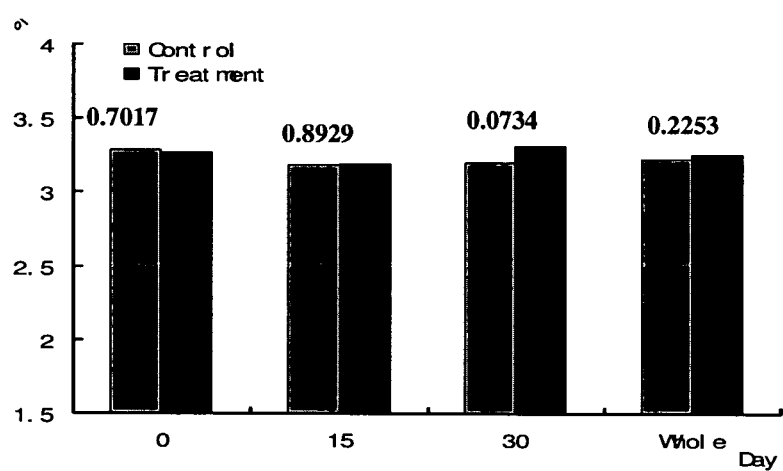
FIG. 16 is a chart of the effects of Enzyme Sample on milk protein (P values are presented in the figure).

Enzyme Sample had no significant effect on milk protein (p>0.05) (FIG. 16), which is consistent with the former trial (Example 11)

Effect of Enzyme Sample on SCC

Figure 17:
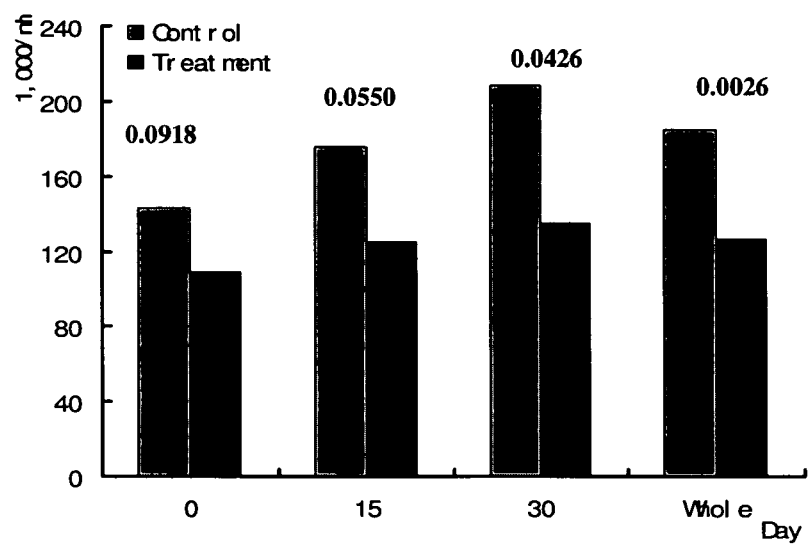
FIG. 17 is a chart of the effects of Enzyme Sample on SCC (P values are presented in the figure).

The effect of Enzyme Sample on SCC is presented in FIG. 17.

No statistical effect was found at the first 15 days of the testing period. However, the SCC was decreased sharply from the 30th day in the treatment group compared with Control (p<0.05). In the entire testing period, SCC was decreased significantly when supplemented with Enzyme Sample (p<0.01), which demonstrated that Enzyme Sample enhanced the health condition of lactating dairy cows. This is consistent with the previous Nanjing trial (Example 11) in which statistical decrease in milk SCC was also observed when supplemented with Enzyme Sample at 1000 g/T concentrate (p<0.05).

Conclusions

In summary, supplementation with Enzyme Sample enhanced the lactation performance in this study. This study shows that Enzyme Sample at 500 g/Ton of concentrate significantly increased milk yield (p<0.01) and milk fat (p<0.05). No effect was obtained in milk protein. SCC was decreased significantly (p<0.01), indicating that Enzyme Sample improved the health condition of dairy cows. ROI of 5.56 was achieved when Enzyme Sample was applied in this trial.

Example 13

Materials and Methods

Enzyme Sample

The Enzyme Sample used in this trial is formula KAC023-19.

Trial Animals

Based on the Days in Milk (DIM) and lactation performance, thirty primiparous lactating Chinese Holstein cows with average live weight 520±6.44 Kg were chosen from a dairy farm in Baotou City, Inner Mongolia and randomly divided into 3 groups, namely Control, Treatment 1 and Treatment 2 with 10 animals each. In the two treatments, Enzyme Sample was added into concentrate at 500 g/Ton and 1000 g/T of concentrate, respectively. The details of trial animals and grouping were given in Table 21.

Concentrate was mixed with silage and forage into a completed diet as a total mixed ration (TMR). The ingredient and nutrient composition of TMR are given in Table 22. The average feed intake of three groups was 35 Kg (Fresh) per head per day. Trial animals were fed twice per day and fresh water was available at all times.

TABLE 21

Experimental design and information of trial animals

|  | Control | Treatment 1 | Treatment 2 |
|---|---|---|---|
| No. of animals | 10 | 10 | 10 |
| Dosage, g/T concentrate | 0 | 500 | 100 |
| Parity | 1.0 | 1.0 | 1.0 |
| DIM | 72.5 | 73.2 | 72.8 |
| Milk yield, Kg/d | 16.51 | 16.52 | 16.49 |
| Milk fat, % | 3.40 | 3.40 | 3.37 |
| Milk protein, % | 2.99 | 2.97 | 3.06 |
| SCC, ×1000/ml | 228 | 225 | 223 |

TABLE 22

Ingredient and nutrient composition of TMR

| Ingredients | %, Fresh wt | Nutrient composition | |
|---|---|---|---|
| Corn silage | 42.54 | NEL (MJ/kg) | 4.26 |
| Corn stalk | 5.26 | DM (%) | 64.10 |
| Corn | 25.92 | CP (%) | 10.31 |
| Wheat bran | 7.61 | ADF (%) | 18.37 |
| Soybean meal | 8.39 | NDF (%) | 32.51 |
| Cottonseed meal | 4.16 | Ca (%) | 0.73 |
| sunflower meal | 2.49 | P (%) | 0.32 |
| Limestone | 1.27 | | |
| Dicalcium phosphate | 0.64 | | |
| Sodium chloride | 0.51 | | |
| Premix | 0.77 | | |
| Sodium carbonate | 0.77 | | |
| Vitamin E | 0.03 | | |
| MgO | 0.21 | | |
| Total | 100.00 | | |

The study was conducted in one-way experiment with 45 days composed of 15 d pretreatment period and 30 d testing period.

Parameters Determined

In the entire experimental period, milk yield was recorded everyday. Milk compositions were determined every two days for analysis of fat, protein, lactose, non-fat solids (NFS). Somatic cell count (SCC) was determined by SCC counting analyzer every week.

Visual observation on the trial animals was conducted everyday, including coat color, body condition, estrus rate and feed intake.

Data Analysis

The data were analyzed by one-way ANOVA using the statistical software SAS (v 6.12, 1996), Duncan's multiple range test was used to resolve the differences among treatment means. Means are different when p<0.05 and significantly difference when p<0.01.

Results and Discussions

Effects of Enzyme Sample on Milk Yield

Figure 18:
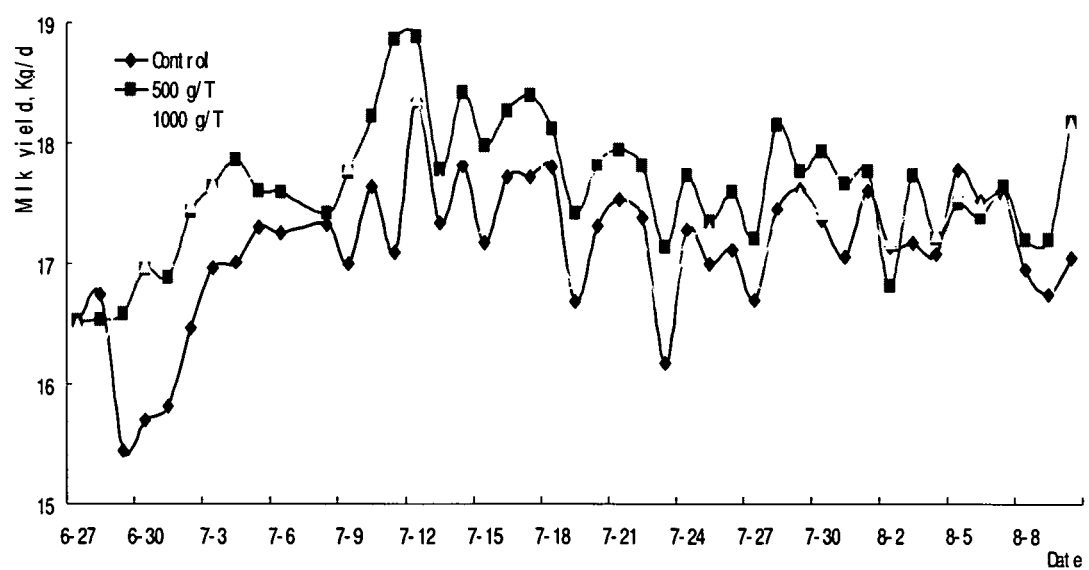
FIG. 18 is a chart of the trend of milk yield in Example 13.

The lactation curve of the entire experimental period is described in FIG. 18. Milk yields of the treatment groups were higher than the Control.

Figure 19:
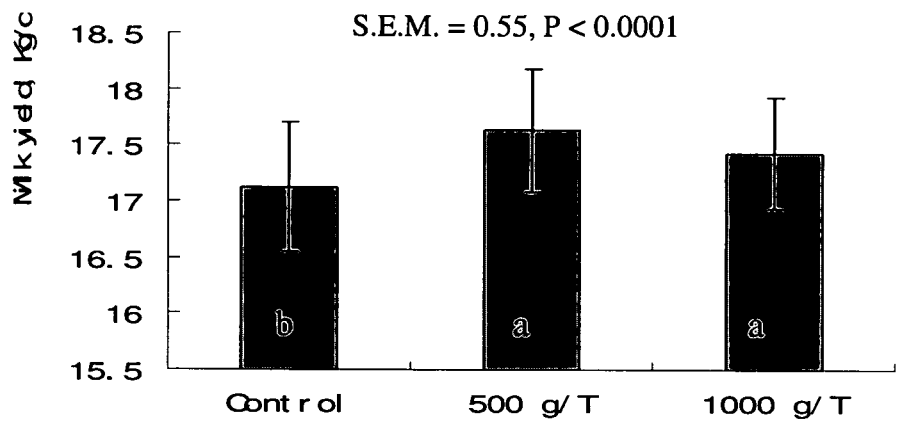
FIG. 19 is a chart of the effects of Enzyme Sample on milk yield (P values are presented in the figure); a,b—means with the different letters within the columns differ significantly (p<0.01).

Statistical results on milk yield were given in FIG. 19. The average milk yield of Treatment 1 and Treatment 2 was increased significantly (p<0.01) by 0.31 and 0.51 kg/d respectively compared with Control (P<0.05), while there was no significant difference between Treatment 1 and Treatment 2 (p>0.05). The difference of two treatment groups was not significant. However, Treatment 2 showed a numerical decrease on milk yield compared with Treatment 1. It indicated that applying of Enzyme Sample at the dosage of 500 g/T has reached the maximum effect of this product on improving milk yield. This conclusion is consistent with the trial conducted in Eastern China (Example 11).

Effects of Enzyme Sample on Milk Components

Figure 20:
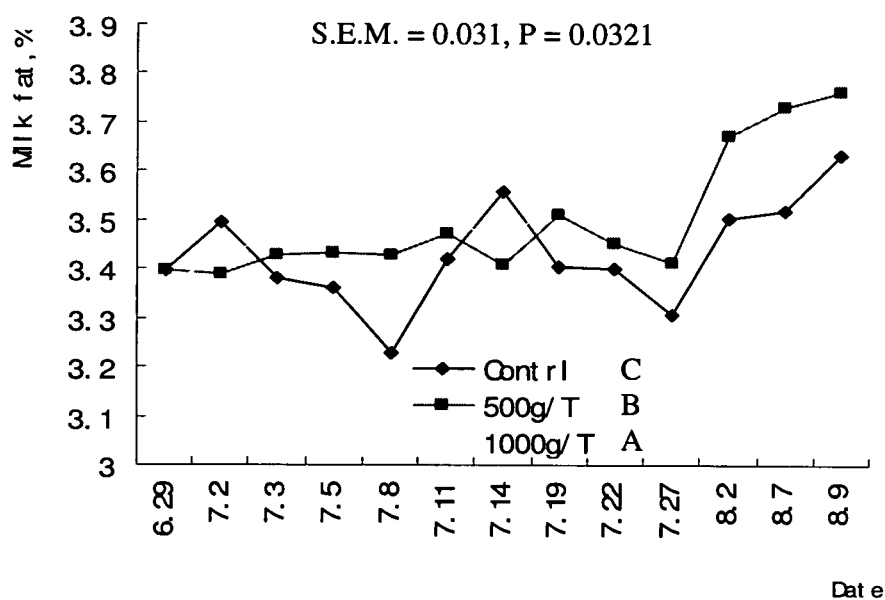
FIG. 20 is a chart of the effects of Enzyme Sample on milk fat (P values are presented in the figure); A,B,C—means with the different letters after the symbols differ (p<0.05).

Effect of Enzyme Sample on milk fat was presented in FIG. 20. Both Treatment 1 and Treatment 2 showed significant increase on milk fat compared with Control (p<0.05) by 2.34% and 4.09%, respectively. The milk fat of Treatment 2 was higher than that of Treatment 1 (p<0.05).

In the former animal trial conducted in Nanjing, Enzyme Sample showed a numerical increase on milk fat (Example 11). And in the animal trial conducted in Liaoning, milk fat was increased significant when treated with Enzyme Sample at the dosage of 500 g/T concentrate (p=0.0230) (Example 12). These results demonstrated that Enzyme Sample can increase the content of milk fat.

Figure 21:
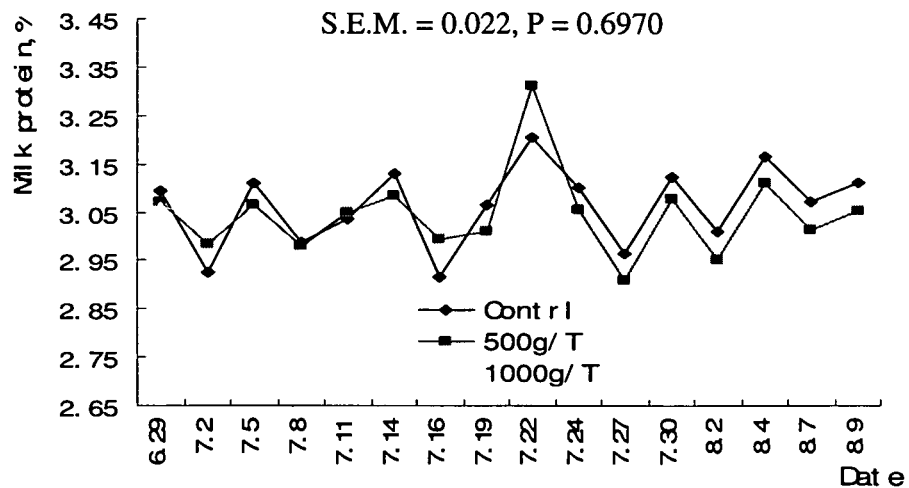
FIG. 21 is a chart of the effects of Enzyme Sample on milk protein (P values are presented in the figure).

Enzyme Sample had no significant effect on milk protein (p>0.05) (FIG. 21), which was consistent with the former trials (Examples 11 and 12)

Figure 22A:
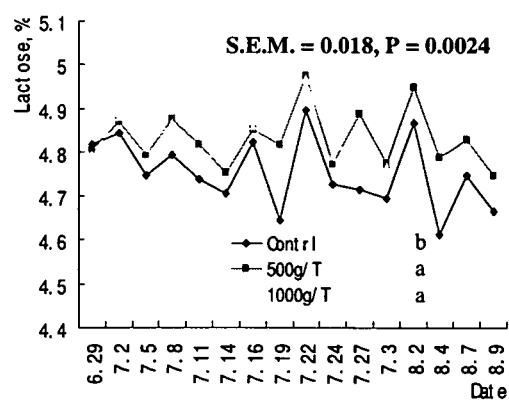
FIGS. 22A and 22B are charts of the effects of Enzyme Sample on lactose (FIG. 22A) and NFS (FIG. 22B) (P values are presented in the figure); a,b—means with the different letters after the symbols differ significantly (p<0.01)
Figure 22B:
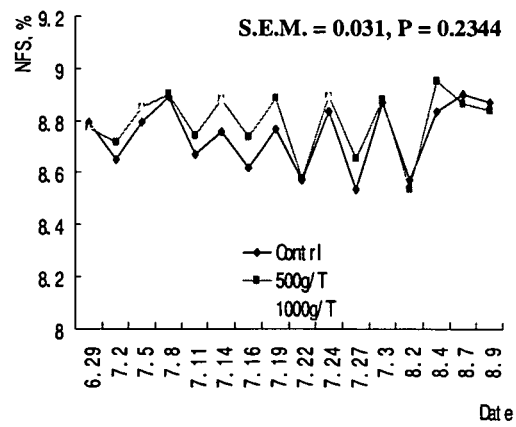

As presented in FIGS. 22A and 22B, the content of lactose in milk was increased significantly (p<0.01) when supplementing with Enzyme Sample at both 500 g/t and 1000 g/T in this study, which suggested that Enzyme Sample might increase the content of lactose. However, this needs more studies to demonstrate.

Consistent with the trial conducted in Nanjing (Example 11), Enzyme Sample showed no significant effect on NFS (p>0.05).

Effect of Enzyme Sample on SCC

Figure 23:
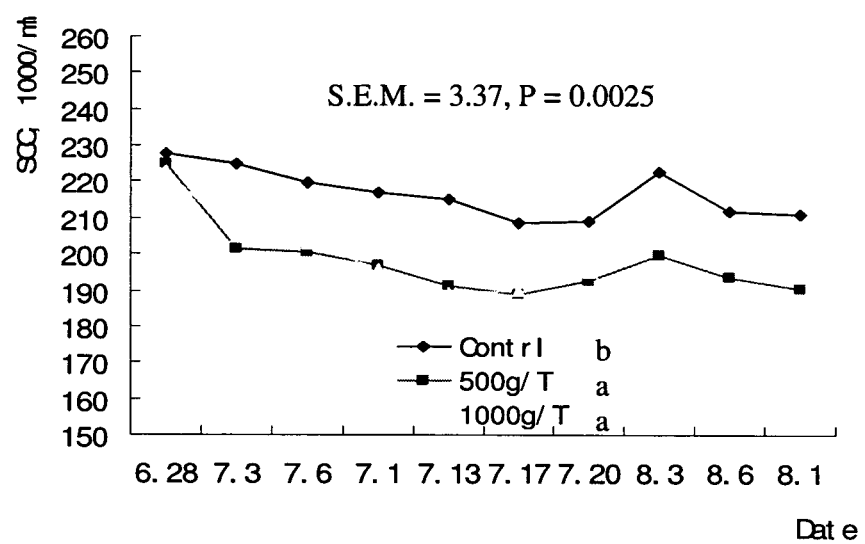
FIG. 23 is a chart of the effects of Enzyme Sample on SCC (P values are presented in the figure); a,b—means with the different letters after the symbols differ significantly (p<0.01).

The effect of Enzyme Sample on SCC was presented in FIG. 23.

SCC of the both treatments decreased sharply compared with Control (p<0.01), and there was no significant difference between the two treatments. Numerically evaluation showed that SCC decreased gradually along with the increase of Enzyme Sample supplementation dosage, which was consistent with the trial conducted in Nanjing (Example 11). In that trial, numerical decrease and statistical decrease (p<0.05) were observed when supplementing with Enzyme Sample at the dosages of 500 g/T and 1000 g/T, respectively. In the trial conducted in Liaoning, the SCC of Treatment (500 g/T) was significantly lower than Control (p<0.01) (Example 12). Based on the results of these three trials, it was concluded that applying Enzyme Sample can decrease the SCC in milk and enhance the health condition of lactating dairy cows.

Visual Observation

The results of visual observation on the trial cows were described in Table 23. The coat, body condition, reproduction and intake of dairy cows were improved through visual observation after treated with Enzyme Sample.

In this study, the trial animals were primiparous, and the body was not completely mature. The body condition in the first parity is very important to the performance of the coming parities. A good body condition means a better potential on productive and reproductive performance. In this study, the body condition was enhanced via visual observation and the body condition score (BCS) was increased significantly when supplementing with Enzyme Sample. Enzyme Sample spurred dairy cows into estrus, which suggested that the reproductive performance was improved. These indicated that the efficiency of dairy cows was improved and more benefits would be obtained.

TABLE 23

Results of visual observation on trial animals

| | Control and early experiment period of treatment groups | Middle and late experiment period of treatment groups |
|---|---|---|
| Coat | Imperfect and dingy, incomplete moult | Tidy, smooth, bright. |
| Body condition | Thin, most BCS < 2.5 | Body condition improved; most BCS > 3.0, even 3.5 |
| Estrus rate | Most non-estrus | About 80□ estrus when the experiment ended |
| Feed intake | Normal Speed, food preference | Rapid feed intake speed, nearly no residual feed |

Conclusions

In summary, supplementation with Enzyme Sample enhanced the lactation performance in this study. This study showed that at both dosages of 500 g/T and 1000 g/T of concentrate, Enzyme Sample significantly increased milk yield (p<0.01), milk fat (p<0.05) and the content of lactose in milk (p<0.01). No effect was obtained in milk protein. SCC was decreased significantly (p<0.01), indicating that Enzyme Sample improved the health condition of dairy cows. In this trial, ROIs of 2.88 and 1.76 were achieved when Enzyme Sample was applied at 500 g/T and 1000 g/T, respectively. Body condition and reproduction improved after treated with Enzyme Sample through visual observation.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method for improving the digestibility of a forage diet for raising mile yield and fat levels in ruminant animals, comprising the steps of:
    (a) selecting a forage from the group consisting of alfalfa, Chinese wildrye, corn silage, straw silage, corn stover, ryegrass and a total mixture ration;
    (b) adding to the forage an enzyme product having cellulase, xylanase, beta-glucanase, pectinase, mannanase and alpha-galactosidase activities;
    (c) excluding enzymes having amylase activity to reduce the risk of acidosis and increase glucose availability to the ruminant animal;
    (d) directly feeding the forage diet to the ruminant animal to reduce non-starch carbohydrates in the forage; and
    (e) raising milk yield and/or fat levels in the ruminant animals.

2. The method as defined in claim 1, wherein the enzyme product is present in an amount to provide between about 200 and about 800 units per gram of activity of cellulase, between about 750 and about 3000 units per gram of activity of xylanase, between about 225 and about 890 units per gram of activity of beta-glucanase, between about 1 and about 100 units per gram of activity of pectinase, between about 50 and about 800 units per gram of activity of beta-mannanase, and between about 1 and about 100 units per gram of activity of alpha-galactosidase.

3. The method of claim 2, wherein the enzyme product is present in an amount to provide between about 200 and about 600 units per gram of activity of cellulase, between about 750 and about 2250 units per gram of activity of xylanase, between about 225 and about 625 units per gram of activity of beta-glucanase, between about 1 and about 5 units per gram of activity of pectinase, between about 100 and about 300 units per gram of activity of beta-mannanase, and between about 1 and about 5 units per gram of activity of alpha-galactosidase.

4. The method of claim 1, wherein the enzyme product is present in an amount to provide between about 125 grams and about 2000 grams per ton of forage.

* * * * *

UNITED STATES PATENT AND TRADEMARK OFFICE
CERTIFICATE OF CORRECTION

| | |
|---|---|
| PATENT NO. | : 8,815,316 B2 |
| APPLICATION NO. | : 12/164706 |
| DATED | : August 26, 2014 |
| INVENTOR(S) | : Duan et al. |

Page 1 of 1

It is certified that error appears in the above-identified patent and that said Letters Patent is hereby corrected as shown below:

In the Claims:

In claim 1, line 2, the term "mile" should read - milk -.

Signed and Sealed this
Twenty-third Day of December, 2014

Michelle K. Lee
*Deputy Director of the United States Patent and Trademark Office*